(12) United States Patent
Dearden et al.

(10) Patent No.: US 9,166,441 B2
(45) Date of Patent: Oct. 20, 2015

(54) MICROPROCESSOR CONTROLLED CLASS E DRIVER

(71) Applicant: ALFRED E. MANN FOUNDATION FOR SCIENTIFIC RESEARCH, Santa Clarita, CA (US)

(72) Inventors: Brian R. Dearden, Pasadena, CA (US); James H. Wolfe, Huntsville, AL (US); Manish Khemani, San Jose, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 0 days.

(21) Appl. No.: 14/593,781

(22) Filed: Jan. 9, 2015

(65) Prior Publication Data

US 2015/0123608 A1    May 7, 2015

Related U.S. Application Data

(63) Continuation of application No. 14/446,294, filed on Jul. 29, 2014.

(60) Provisional application No. 61/859,471, filed on Jul. 29, 2013.

(51) Int. Cl.
*H02J 7/00* (2006.01)
*H02J 7/02* (2006.01)
(Continued)

(52) U.S. Cl.
CPC ............ *H02J 7/025* (2013.01); *A61N 1/36125* (2013.01); *A61N 1/3727* (2013.01);
(Continued)

(58) Field of Classification Search
CPC ........... A61N 1/36021; A61N 1/36014; A61N 1/36071; A61N 1/3605; A61N 1/36017; A61N 1/3708; A61N 1/378; A61N 1/08; G01R 31/3648; G01R 31/3662

USPC ......................................................... 320/108
See application file for complete search history.

(56) References Cited

U.S. PATENT DOCUMENTS 3,942,535 A  3/1976 Schulman
4,082,097 A  4/1978 Mann et al.
(Continued)

FOREIGN PATENT DOCUMENTS

DE   102010006837 A1   8/2011
EP   1680182            7/2006
(Continued)

OTHER PUBLICATIONS

Boiocchi, S., et al., "Self-calibration in high speed current steering CMOS D/A converters", Advanced A-D and D-A Conversion Techniques and Their Applications, 1994, Second International Conference on Cambridge, UK, London, UK, IEE, UK, Jan. 1, 1994, pp. 148-152.

(Continued)

*Primary Examiner* — Arun Williams
(74) *Attorney, Agent, or Firm* — Kilpatrick Townsend & Stockton LLP

(57) ABSTRACT

A charger including a class E power driver, a frequency-shift keying ("FSK") module, and a processor. The processor can receive data relating to the operation of the class E power driver and can control the class E power driver based on the received data relating to the operation of the class E power driver. The processor can additionally control the FSK module to modulate the natural frequency of the class E power transformer to thereby allow the simultaneous recharging of an implantable device and the simultaneous transmission of data to the implantable device. The processor can additionally compensate for propagation delays by adjusting switching times.

18 Claims, 11 Drawing Sheets

(51) Int. Cl.
  *H03C 3/00* (2006.01)
  *H04B 5/00* (2006.01)
  *A61N 1/378* (2006.01)
  *A61N 1/372* (2006.01)
  *A61N 1/36* (2006.01)

(52) U.S. Cl.
  CPC .......... *A61N1/3787* (2013.01); *A61N 1/37223* (2013.01); *H02J 7/007* (2013.01); *H02J 7/0052* (2013.01); *H03C 3/00* (2013.01); *H04B 5/0037* (2013.01); *H02J 2007/0096* (2013.01)

(56) References Cited

U.S. PATENT DOCUMENTS

| | | | |
|---|---|---|---|
| 4,468,723 A | 8/1984 | Hughes | |
| 4,673,867 A | 6/1987 | Davis | |
| 5,143,089 A | 9/1992 | Alt | |
| 5,193,539 A | 3/1993 | Schulman et al. | |
| 5,690,693 A | 11/1997 | Wang et al. | |
| 5,702,431 A | 12/1997 | Wang et al. | |
| 5,735,887 A | 4/1998 | Barreras, Sr. et al. | |
| 5,741,316 A | 4/1998 | Chen et al. | |
| 5,876,423 A | 3/1999 | Braun | |
| 5,877,472 A | 3/1999 | Campbell et al. | |
| 6,035,237 A | 3/2000 | Schulman et al. | |
| 6,055,456 A | 4/2000 | Gerber | |
| 6,057,513 A | 5/2000 | Ushikoshi et al. | |
| 6,067,474 A | 5/2000 | Schulman et al. | |
| 6,076,017 A | 6/2000 | Taylor et al. | |
| 6,164,284 A | 12/2000 | Schulman et al. | |
| 6,178,353 B1 | 1/2001 | Griffith et al. | |
| 6,185,452 B1 | 2/2001 | Schulman et al. | |
| 6,191,365 B1 | 2/2001 | Avellanet | |
| 6,208,894 B1 | 3/2001 | Schulman et al. | |
| 6,212,431 B1 | 4/2001 | Hahn et al. | |
| 6,221,513 B1 | 4/2001 | Lasater | |
| 6,246,911 B1 | 6/2001 | Seligman | |
| 6,265,789 B1 | 7/2001 | Honda et al. | |
| 6,313,779 B1 | 11/2001 | Leung et al. | |
| 6,315,721 B2 | 11/2001 | Schulman et al. | |
| 6,427,086 B1 | 7/2002 | Fischell et al. | |
| 6,438,423 B1 | 8/2002 | Rezai et al. | |
| 6,442,434 B1 | 8/2002 | Zarinetchi et al. | |
| 6,505,075 B1 | 1/2003 | Weiner | |
| 6,516,227 B1 | 2/2003 | Meadows et al. | |
| 6,521,350 B2 | 2/2003 | Fey et al. | |
| 6,564,807 B1 | 5/2003 | Schulman et al. | |
| 6,584,355 B2 | 6/2003 | Stessman | |
| 6,600,954 B2 | 7/2003 | Cohen et al. | |
| 6,609,032 B1 | 8/2003 | Woods et al. | |
| 6,721,603 B2 | 4/2004 | Zabara et al. | |
| 6,735,474 B1 | 5/2004 | Loeb et al. | |
| 6,745,077 B1 | 6/2004 | Griffith et al. | |
| 6,809,701 B2 | 10/2004 | Amundson et al. | |
| 6,836,684 B1 | 12/2004 | Rijkhoff et al. | |
| 6,864,755 B2 | 3/2005 | Moore | |
| 6,892,098 B2 | 5/2005 | Ayal et al. | |
| 6,895,280 B2 | 5/2005 | Meadows et al. | |
| 6,901,287 B2 | 5/2005 | Davis et al. | |
| 6,986,453 B2 | 1/2006 | Jiang et al. | |
| 6,989,200 B2 | 1/2006 | Byers et al. | |
| 6,990,376 B2 | 1/2006 | Tanagho et al. | |
| 7,051,419 B2 | 5/2006 | Schrom et al. | |
| 7,069,081 B2 | 6/2006 | Biggs et al. | |
| 7,114,502 B2 | 10/2006 | Schulman et al. | |
| 7,127,298 B1 | 10/2006 | He et al. | |
| 7,142,925 B1 | 11/2006 | Bhadra et al. | |
| 7,177,690 B2 | 2/2007 | Woods et al. | |
| 7,191,005 B2 | 3/2007 | Stessman | |
| 7,212,110 B1 | 5/2007 | Martin et al. | |
| 7,225,032 B2 | 5/2007 | Schmeling et al. | |
| 7,234,853 B2 | 6/2007 | Givoletti | |
| 7,245,972 B2 | 7/2007 | Davis | |
| 7,286,880 B2 | 10/2007 | Olson et al. | |
| 7,317,948 B1 | 1/2008 | King et al. | |
| 7,324,852 B2 | 1/2008 | Barolat et al. | |
| 7,324,853 B2 | 1/2008 | Ayal et al. | |
| 7,328,068 B2 | 2/2008 | Spinelli et al. | |
| 7,331,499 B2 | 2/2008 | Jiang et al. | |
| 7,369,894 B2 | 5/2008 | Gerber | |
| 7,386,348 B2 | 6/2008 | North et al. | |
| 7,396,265 B2 | 7/2008 | Darley et al. | |
| 7,444,181 B2 | 10/2008 | Shi et al. | |
| 7,450,991 B2 | 11/2008 | Smith et al. | |
| 7,460,911 B2 | 12/2008 | Cosendai et al. | |
| 7,483,752 B2 | 1/2009 | Von Arx et al. | |
| 7,496,404 B2 | 2/2009 | Meadows et al. | |
| 7,513,257 B2 | 4/2009 | Schulman et al. | |
| 7,515,967 B2 | 4/2009 | Phillips et al. | |
| 7,532,936 B2 | 5/2009 | Erickson et al. | |
| 7,539,538 B2 | 5/2009 | Parramon et al. | |
| 7,555,346 B1 | 6/2009 | Woods et al. | |
| 7,565,203 B2 | 7/2009 | Greenberg et al. | |
| 7,636,602 B2 | 12/2009 | Baru Fassio et al. | |
| 7,643,880 B2 | 1/2010 | Tanagho et al. | |
| 7,720,547 B2 | 5/2010 | Denker et al. | |
| 7,725,191 B2 | 5/2010 | Greenberg et al. | |
| 7,734,355 B2 | 6/2010 | Cohen et al. | |
| 7,738,965 B2 | 6/2010 | Phillips et al. | |
| 7,771,838 B1 | 8/2010 | He et al. | |
| 7,774,069 B2 | 8/2010 | Olson et al. | |
| 7,813,803 B2 | 10/2010 | Heruth et al. | |
| 7,813,809 B2 | 10/2010 | Strother et al. | |
| 7,826,901 B2 | 11/2010 | Lee et al. | |
| 7,848,818 B2 | 12/2010 | Barolat et al. | |
| 7,904,167 B2 | 3/2011 | Klosterman et al. | |
| 7,925,357 B2 | 4/2011 | Phillips et al. | |
| 7,932,696 B2 | 4/2011 | Peterson | |
| 7,952,349 B2 | 5/2011 | Huang et al. | |
| 7,957,818 B2 | 6/2011 | Swoyer | |
| 7,979,119 B2 | 7/2011 | Kothandaraman et al. | |
| 7,979,126 B2 | 7/2011 | Payne et al. | |
| 7,988,507 B2 | 8/2011 | Darley et al. | |
| 8,000,805 B2 | 8/2011 | Swoyer et al. | |
| 8,005,549 B2 | 8/2011 | Boser et al. | |
| 8,005,550 B2 | 8/2011 | Boser et al. | |
| 8,019,423 B2 | 9/2011 | Possover | |
| 8,024,047 B2 | 9/2011 | Olson et al. | |
| 8,036,756 B2 | 10/2011 | Swoyer et al. | |
| 8,044,635 B2 | 10/2011 | Peterson | |
| 8,055,337 B2 | 11/2011 | Moffitt et al. | |
| 8,103,360 B2 | 1/2012 | Foster | |
| 8,121,701 B2 | 2/2012 | Woods et al. | |
| 8,129,942 B2 | 3/2012 | Park et al. | |
| 8,131,358 B2 | 3/2012 | Moffitt et al. | |
| 8,140,168 B2 | 3/2012 | Olson et al. | |
| 8,175,717 B2 | 5/2012 | Haller et al. | |
| 8,180,452 B2 | 5/2012 | Shaquer | |
| 8,214,042 B2 * | 7/2012 | Ozawa et al. | 607/29 |
| 8,219,196 B2 | 7/2012 | Torgerson | |
| 8,219,202 B2 | 7/2012 | Giftakis et al. | |
| 8,255,057 B2 | 8/2012 | Fang et al. | |
| 8,314,594 B2 | 11/2012 | Scott et al. | |
| 8,332,040 B1 | 12/2012 | Winstrom | |
| 8,362,742 B2 | 1/2013 | Kallmyer | |
| 8,369,943 B2 | 2/2013 | Shuros et al. | |
| 8,386,048 B2 | 2/2013 | McClure et al. | |
| 8,417,346 B2 | 4/2013 | Giftakis et al. | |
| 8,423,146 B2 | 4/2013 | Giftakis et al. | |
| 8,447,402 B1 | 5/2013 | Jiang et al. | |
| 8,447,408 B2 | 5/2013 | North et al. | |
| 8,457,756 B2 | 6/2013 | Rahman | |
| 8,457,758 B2 | 6/2013 | Olson et al. | |
| 8,515,545 B2 | 8/2013 | Trier | |
| 8,538,530 B1 | 9/2013 | Orinski | |
| 8,549,015 B2 | 10/2013 | Barolat | |
| 8,554,322 B2 | 10/2013 | Olson et al. | |
| 8,555,894 B2 | 10/2013 | Schulman et al. | |
| 8,577,474 B2 | 11/2013 | Rahman et al. | |
| 8,588,917 B2 | 11/2013 | Whitehurst et al. | |
| 8,612,002 B2 | 12/2013 | Faltys et al. | |
| 8,620,436 B2 | 12/2013 | Parramon et al. | |
| 8,700,175 B2 | 4/2014 | Fell | |

(56) References Cited

U.S. PATENT DOCUMENTS

| | | |
|---|---|---|
| 8,750,985 B2 | 6/2014 | Parramon et al. |
| 2002/0116042 A1 | 8/2002 | Boling |
| 2003/0028072 A1* | 2/2003 | Fischell et al. .................. 600/13 |
| 2003/0078633 A1 | 4/2003 | Firlik et al. |
| 2004/0106963 A1 | 6/2004 | Tsukamoto et al. |
| 2005/0104577 A1 | 5/2005 | Matei et al. |
| 2006/0016452 A1 | 1/2006 | Goetz et al. |
| 2006/0050539 A1 | 3/2006 | Yang et al. |
| 2006/0142822 A1 | 6/2006 | Tulgar |
| 2006/0206166 A1 | 9/2006 | Weiner |
| 2007/0073357 A1 | 3/2007 | Rooney et al. |
| 2007/0293914 A1 | 12/2007 | Woods et al. |
| 2008/0132961 A1 | 6/2008 | Jaax et al. |
| 2008/0172109 A1 | 7/2008 | Rahman et al. |
| 2008/0278974 A1* | 11/2008 | Wu .............................. 363/21.18 |
| 2009/0088816 A1 | 4/2009 | Harel et al. |
| 2009/0105785 A1 | 4/2009 | Wei et al. |
| 2009/0112291 A1 | 4/2009 | Wahlstrand et al. |
| 2009/0259273 A1 | 10/2009 | Figueiredo et al. |
| 2010/0076534 A1 | 3/2010 | Mock |
| 2011/0152959 A1 | 6/2011 | Sherwood et al. |
| 2011/0270269 A1 | 11/2011 | Swoyer et al. |
| 2011/0278948 A1 | 11/2011 | Forsell |
| 2011/0301667 A1 | 12/2011 | Olson et al. |
| 2012/0016447 A1 | 1/2012 | Zhu et al. |
| 2012/0041512 A1 | 2/2012 | Weiner |
| 2012/0046712 A1 | 2/2012 | Woods et al. |
| 2012/0071950 A1 | 3/2012 | Archer |
| 2012/0119698 A1 | 5/2012 | Karalis et al. |
| 2012/0130448 A1 | 5/2012 | Woods et al. |
| 2012/0259381 A1 | 10/2012 | Smith et al. |
| 2012/0262108 A1 | 10/2012 | Olson et al. |
| 2012/0274270 A1 | 11/2012 | Dinsmoor et al. |
| 2013/0023958 A1 | 1/2013 | Fell |
| 2013/0096651 A1 | 4/2013 | Ozawa et al. |
| 2013/0148768 A1* | 6/2013 | Kim .............................. 375/354 |
| 2013/0150925 A1 | 6/2013 | Vamos et al. |
| 2013/0211479 A1 | 8/2013 | Olson et al. |
| 2013/0303942 A1 | 11/2013 | Damaser et al. |
| 2014/0277268 A1 | 9/2014 | Lee et al. |
| 2014/0277270 A1 | 9/2014 | Parramon et al. |

FOREIGN PATENT DOCUMENTS

| | | |
|---|---|---|
| EP | 1904153 | 4/2008 |
| EP | 2243509 | 10/2010 |
| JP | 2003047179 A | 2/2003 |
| WO | WO 00/66221 A1 | 11/2000 |
| WO | WO 02/03408 A2 | 1/2002 |
| WO | WO02/09808 A1 | 2/2002 |
| WO | WO 2004/103465 A1 | 12/2004 |
| WO | WO 2008/021524 | 2/2008 |
| WO | WO 2009/051539 A1 | 4/2009 |
| WO | WO 2009/091267 A2 | 7/2009 |
| WO | WO 2010/042056 A1 | 4/2010 |
| WO | WO 2010/042057 A1 | 4/2010 |
| WO | WO 2011/059565 | 5/2011 |
| WO | WO 2013/141884 | 9/2013 |

OTHER PUBLICATIONS

Gundason, G., "A low-power ASK demodulator for Inductively coupled implantable electronics", Solid-State Circuits Conference, 2000, Esscirc 00, Proceedings of the 26RD European, IEEE, Sep. 19, 2000, pp. 385-388.

Humayun, M.S., et al., "A Variable Range Bi-Phasic Current Stimulus Driver Circuitry for an Implantable Retinal Prosthetic Device", IEEE Journal of Solid-State Circuits, IEEE Service Center, Piscataway, NJ, USA, vol. 40, No. 3, Mar. 1, 2005, pp. 763-771.

Van Paemel, M., "High-Efficiency Transmission for Medical Implants", IEEE Solid-State Circuits Magazine, IEEE, USA, vol. 3, No. 1, Jan. 1, 2011, pp. 47-59.

Wang, Chua-Chin, et al., "A 140-dB CMRR Low-noise Instrumentation Amplifier for Neural Signal Sensing", Circutis and Systems, 2006, APCCAS 2006, IEEE Asia Pacific Conference on IEEE, Piscataway, NJ, USA, Dec. 1, 2006, pp. 696-699.

* cited by examiner

MICROPROCESSOR CONTROLLED CLASS E DRIVER

CROSS-REFERENCES TO RELATED APPLICATIONS

This application is a continuation of U.S. patent application Ser. No. 14/446,294, filed on Jul. 29, 2014, which claims the benefit of U.S. Provisional Application No. 61/859,471 entitled "MICROPROCESSOR CONTROLLED CLASS E DRIVER," and filed on Jul. 29, 2013, the entirety of which is hereby incorporated by reference herein.

BACKGROUND OF THE INVENTION

The prevalence of use of medical devices in treating ailments is increasing with time. In many instances, and as these medical devices are made smaller, these medical devices are frequently implanted within a patient. While the desirability of implantable devices is increasing as the size of the devices has decreased, the implantation process still frequently requires complicated surgery which can expose the patient to significant risks and protracted recovery times. In light of this, further methods, systems, and devices are desired to increase the ease of implantation of medical devices, and the ease of use of such implanted medical devices.

BRIEF SUMMARY OF THE INVENTION

One aspect of the present disclosure relates to a charger. The charger includes a charging coil, which charging coil is configured to magnetically couple with an implantable device to recharge the implantable device, a class E driver electrically connected to the charging coil, which class E driver includes a switching circuit that is switched by the application of a first voltage to the switching circuit, and a current sensor positioned to sense a current passing through the charging coil. The charger can include a processor electrically connected to the class E driver to receive data indicative of the current passing through the charging coil and electrically connected to the class E driver to control the switching circuit via the application of the first voltage to the switching circuit. In some embodiments, the processor can receive data indicative of the current passing through the charging coil and control the switching circuit in response to the received data.

In some embodiments, the switching circuit can be a transistor. In some embodiments, the transistor can be a MOSFET. In some embodiments, the processor is electrically connected to the class E driver to receive data indicative of a second voltage of the switching circuit. In some embodiments, the processor can receive data indicative of the second voltage of the switching circuit, and control the switching circuit in response to the received data indicative of the second voltage of the switching circuit.

In some embodiments, the second voltage is measured at the drain of the switching circuit and the first voltage is applied to the gate of the switching circuit. In some embodiments, the processor is electrically connected to the class E driver via a voltage divider including a first resistor and a second resistor. In some embodiments, the processor can sense a power switching transistor voltage, and determine whether to adjust a first frequency with which the first voltage is applied to the switching circuit, which adjustment of the first frequency mitigates one or several propagation delays.

In some embodiments, the processor can retrieve a stored value identifying a second frequency with which the first voltage is applied based on the sensed power switching transistor voltage. In some embodiments, the processor can compare the retrieved stored value identifying the second frequency with which the first voltage is applied to one or several frequency limits. In some embodiments, the first frequency is set to the second frequency if the second frequency does not exceed the one or several frequency limits. In some embodiments, when the second frequency exceeds one of the one or several frequency limits, the first frequency is set to the exceeded one of the one or several frequency limits.

One aspect of the present disclosure relates to a charger. The charger includes a charging coil that can generate a magnetic field having a frequency and can magnetically couple with an implantable device to recharge the implantable device, a class E driver electrically connected to the charging coil, and an FSK module that can modulate the frequency of the magnetic field among at least three frequencies.

In some embodiments, the at least three frequencies include a first frequency, a second frequency, and a third frequency. In some embodiments, the third frequency is the highest frequency and the second frequency is the lowest frequency. In some embodiments, the charger includes a processor electrically connected to the FSK module and that can control the FSK module. In some embodiments, the processor can selectively operate the charger in either a data non-transmitting state or in a data transmitting state.

In some embodiments, a carrier signal has the first frequency when the charger operates in the data non-transmitting state. In some embodiments, the processor controls the FSK module to modulate the carrier signal between the second frequency and the third frequency when the charger operates in the data transmitting state.

In some embodiments, the FSK module includes two capacitors and two transistors. In some embodiments, the two capacitors and the two transistors of the FSK module are electrically connected such that the two capacitors can be selectively included within the circuit by the FSK module. In some embodiments, the processor can control the two transistors of the FSK module to selectively include the two capacitors within the circuit by the FSK module. In some embodiments, the selective inclusion of the two capacitors within the circuit of the FSK modulates the frequency of the magnetic field between the first, second, and third frequencies.

One aspect of the present disclosure relates to a method of communicating with an implantable device during charging of the implantable device. The method includes generating a charging signal with a charging coil, which charging signal has an initial, first frequency, and transmitting data by modulating the frequency of the charging signal between a second frequency that is lower than the first frequency and a third frequency that is higher than the first frequency.

In some embodiments, the method can include generating transmission data, which can be the data that is transmitted. In some embodiments, the transmission data can be in binary format. In some embodiments, modulating the frequency of the charging signal between the second frequency and the third frequency transmits the transmission data in binary format.

In some embodiments, the frequency of the charging signal is modulated by an FSK module. In some embodiments, the FSK module can include two capacitors and two transistors. In some embodiments, the two capacitors and the two transistors of the FSK module are electrically connected such that the two capacitors can be selectively included within the circuit of by the FSK module to thereby modulate the frequency of the charging signal.

One aspect of the present disclosure relates to a method of controlling a charger. The method includes creating a magnetic coupling between a charger and an implantable device, which magnetic coupling charges the implantable device, setting an initial frequency of a drive signal, which frequency of the drive signal is set by a processor, and which drive signal controls the opening and closing of a switch, sensing a voltage at the switch at a first time, based on the voltage at the switch at the first time, retrieving a value identifying a second frequency, and changing the frequency of the drive signal.

In some embodiments, changing the frequency of the drive signal can include changing the frequency of the drive signal from the first frequency to the second frequency. In some embodiments, the method can include retrieving one or several frequency limits, which frequency limits provide an upper and lower bound to a range of acceptable frequencies of the drive signal. In some embodiments, the method can include comparing the second frequency to the one or several frequency limits.

In some embodiments, changing the frequency of the drive signal can include changing the frequency of the drive signal from the first frequency to the one of the one or several frequency limits if the second frequency exceeds the one of the one or several frequency limits. In some embodiments, changing the frequency of the drive signal can include changing the frequency of the drive signal from the first frequency to the second frequency if the second frequency does not exceed the one or several frequency limits. In some embodiments, changing of the frequency of the drive signal can mitigate an effect of a propagation delay. In some embodiments, the frequency of the drive signal can be adjusted multiple times to mitigate the effect of the propagation delay.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

Figure 1:
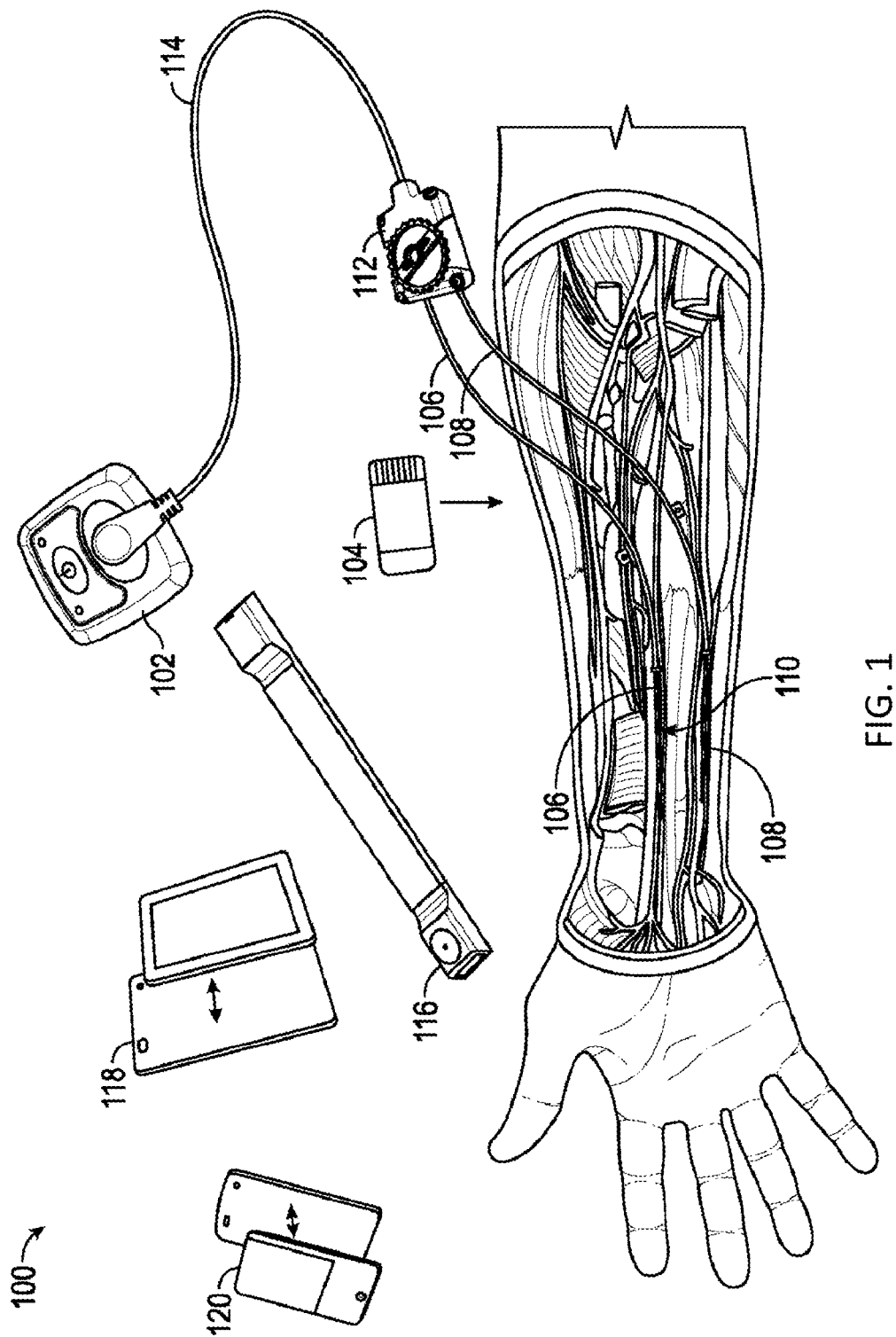
FIG. 1 is a schematic illustration of one embodiment of an implantable neurostimulation system.

In the appended figures, similar components and/or features may have the same reference label. Where the reference label is used in the specification, the description is applicable to any one of the similar components having the same reference label.

DETAILED DESCRIPTION OF THE INVENTION

A significant percentage of the Western (EU and US) population is affected by Neuropathic pain (chronic intractable pain due to nerve damage). In many people, this pain is severe. There are thousands of patients that have chronic intractable pain involving a nerve. Neuropathic pain can be very difficult to treat with only half of patients achieving partial relief Thus, determining the best treatment for individual patients remains challenging. Conventional treatments include certain antidepressants, anti-epileptic drugs and opioids. However, side effects from these drugs can be detrimental. In some of these cases, electrical stimulation can provide effective treatment of this pain without the drug-related side effects.

A spinal cord stimulator is a device used to deliver pulsed electrical signals to the spinal cord to control chronic pain. Because electrical stimulation is a purely electrical treatment and does not cause side effects similar to those caused by drugs, an increasing number of physicians and patients favor the use of electrical stimulation over drugs as a treatment for pain. The exact mechanisms of pain relief by spinal cord stimulation (SCS) are unknown. Early SCS trials were based on the Gate Control Theory, which posits that pain is transmitted by two kinds of afferent nerve fibers. One is the larger myelinated Aδ fiber, which carries quick, intense-pain messages. The other is the smaller, unmyelinated "C" fiber, which transmits throbbing, chronic pain messages. A third type of nerve fiber, called Aβ, is "non-nociceptive," meaning it does not transmit pain stimuli. The gate control theory asserts that signals transmitted by the Aδ and C pain fibers can be thwarted by the activation/stimulation of the non-nociceptive Aβ fibers and thus inhibit an individual's perception of pain. Thus, neurostimulation provides pain relief by blocking the pain messages before they reach the brain.

SCS is often used in the treatment of failed back surgery syndrome, a chronic pain syndrome that has refractory pain due to ischemia. SCS complications have been reported in a large portion, possibly 30% to 40%, of all SCS patients. This increases the overall costs of patient pain management and decreases the efficacy of SCS. Common complications include: infection, hemorrhaging, injury of nerve tissue, placing device into the wrong compartment, hardware malfunction, lead migration, lead breakage, lead disconnection, lead erosion, pain at the implant site, generator overheating, and charger overheating. The occurrence rates of common complications are surprisingly high: including lead extension connection issues, lead breakage, lead migration and infection.

Peripheral neuropathy, another condition that can be treated with electrical stimulation, may be either inherited or acquired. Causes of acquired peripheral neuropathy include physical injury (trauma) to a nerve, viruses, tumors, toxins, autoimmune responses, nutritional deficiencies, alcoholism, diabetes, and vascular and metabolic disorders. Acquired peripheral neuropathies are grouped into three broad categories: those caused by systemic disease, those caused by trauma, and those caused by infections or autoimmune disorders affecting nerve tissue. One example of an acquired peripheral neuropathy is trigeminal neuralgia, in which damage to the trigeminal nerve (the large nerve of the head and face) causes episodic attacks of excruciating, lightning-like pain on one side of the face.

A high percentage of patients with peripheral neuropathic pain do not benefit from SCS for various reasons. However, many of these patients can receive acceptable levels of pain relief via direct electrical stimulation to the corresponding peripheral nerves. This therapy is called peripheral nerve stimulation (PNS). As FDA approved PNS devices have not been commercially available in the US market, Standard spinal cord stimulator (SCS) devices are often used off label by pain physicians to treat this condition. A significant portion of SCS devices that have been sold may have been used off-label for PNS.

As current commercially-available SCS systems were designed for stimulating the spinal cord and not for peripheral nerve stimulation, there are more device complications associated with the use of SCS systems for PNS than for SCS. Current SCS devices (generators) are large and bulky. In the event that an SCS is used for PNS, the SCS generator is typically implanted in the abdomen or in the lower back above the buttocks and long leads are tunneled across multiple joints to reach the target peripheral nerves in the arms, legs or face. The excessive tunneling and the crossing of joints leads to increased post-surgical pain and higher device failure rates. Additionally, rigid leads can lead to skin erosion and penetration, with lead failure rates being far too high within the first few years of implantation. Many or even most complications result in replacement surgery and even multiple replacement surgeries in some cases.

One embodiment of an implantable neurostimulation system 100 is shown in FIG. 1, which implantable neurostimulation system 100 can be, for example, a peripherally-implantable neurostimulation system 100. In some embodiments, the implantable neurostimulation system 100 can be used in treating patients with, for example, chronic, severe, refractory neuropathic pain originating from peripheral nerves. In some embodiments, the implantable neurostimulation system 100 can be used to either stimulate a target peripheral nerve or the posterior epidural space of the spine.

The implantable neurostimulation system 100 can include one or several pulse generators. The pulse generators can comprise a variety of shapes and sizes, and can be made from a variety of materials. In some embodiments, the one or several pulse generators can generate one or several non-ablative electrical pulses that are delivered to a nerve to control pain. In some embodiments, these pulses can have a pulse amplitude of between 0-1,000 mA, 0-100 mA, 0-50 mA, 0-25 mA, and/or any other or intermediate range of amplitudes. One or more of the pulse generators can include a processor and/or memory. In some embodiments, the processor can provide instructions to and receive information from the other components of the implantable neurostimulation system 100. The processor can act according to stored instructions, which stored instructions can be located in memory, associated with the processor, and/or in other components of the implantable neurostimulation system 100. The processor can, in accordance with stored instructions, make decisions. The processor can comprise a microprocessor, such as a microprocessor from Intel® or Advanced Micro Devices, Inc.®, or the like.

In some embodiments, the stored instructions directing the operation of the processor may be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks may be stored in a machine readable medium such as a storage medium. A code segment or machine-executable instruction may represent a procedure, a function, a subprogram, a program, a routine, a subroutine, a module, a software package, a script, a class, or any combination of instructions, data structures, and/or program statements. A code segment may be coupled to another code segment or a hardware circuit by passing and/or receiving information, data, arguments, parameters, and/or memory contents. Information, arguments, parameters, data, etc. may be passed, forwarded, or transmitted via any suitable means including memory sharing, message passing, token passing, network transmission, etc.

In some embodiments, the memory of one or both of the pulse generators can be the storage medium containing the stored instructions. The memory may represent one or more memories for storing data, including read only memory (ROM), random access memory (RAM), magnetic RAM, core memory, magnetic disk storage mediums, optical storage mediums, flash memory devices and/or other machine readable mediums for storing information. In some embodiments, the memory may be implemented within the processor or external to the processor. In some embodiments, the memory can be any type of long term, short term, volatile, nonvolatile, or other storage medium and is not to be limited to any particular type of memory or number of memories, or type of media upon which memory is stored. In some embodiments, the memory can include, for example, one or both of volatile and nonvolatile memory. In one specific embodiment, the memory can include a volatile portion such as RAM memory, and a nonvolatile portion such as flash memory.

In some embodiments, one of the pulse generators can be an external pulse generator 102 or an implantable pulse generator 104. The external pulse generator 102 can be used to evaluate the suitability of a patient for treatment with the implantable neurostimulation system 100 and/or for implantation of an implantable pulse generator 104.

In some embodiments, one of the pulse generators can be the implantable pulse generator 104, which can be sized and shaped, and made of material to allow implantation of the implantable pulse generator 104 inside of a body. In some embodiments, the implantable pulse generator 104 can be sized and shaped so as to allow placement of the implantable pulse generator 104 at any desired location in a body, and in some embodiments, placed proximate to a peripheral nerve such that leads (discussed below) are not tunneled across joints and/or such that extension cables are not needed.

The implantable pulse generator 104 can include one or several energy storage features. In some embodiments, these features can be configured to store energy, such as, for example, electric energy, that can be used in the operation of the implantable pulse generator 104. These energy storage features can include, for example, one or several batteries, including rechargeable batteries, one or several capacitors, one or several fuel cells, or the like.

In some embodiments, the electrical pulses generated by the pulse generator can be delivered to one or several nerves 110 and/or to tissue proximate to one or several nerves 110 via one or several leads. The leads can include conductive portions, such as electrodes or contact portions of electrodes, and non-conductive portions. The leads can have a variety of shapes, can be a variety of sizes, and can be made from a variety of materials, which size, shape, and materials can be dictated by the application or other factors.

In some embodiments, the leads can include an anodic lead 106 and/or a cathodic lead 108. In some embodiments, the anodic lead 106 and the cathodic lead 108 can be identical leads, but can receive pulses of different polarity from the pulse generator.

In some embodiments, the leads can connect directly to the pulse generator, and in some embodiments, the leads can be connected to the pulse generator via a connector 112 and a connector cable 114. The connector 112 can comprise any device that is able to electrically connect the leads to the connector cable 114. Likewise, the connector cable can be any device capable of transmitting distinct electrical pulses to the anodic lead 106 and the cathodic lead 108.

In some embodiments, the implantable neurostimulation system 100 can include a charger 116 that can be configured to recharge the implantable pulse generator 104 when the implantable pulse generator 104 is implanted within a body. The charger 116 can comprise a variety of shapes, sizes, and features, and can be made from a variety of materials. Like the pulse generators 102, 104, the charger 116 can include a processor and/or memory having similar characteristics to those discussed above. In some embodiments, the charger 116 can recharge the implantable pulse generator 104 via an inductive coupling.

In some embodiments, one or several properties of the electrical pulses can be controlled via a controller. In some embodiments, these properties can include, for example, the frequency, strength, pattern, duration, or other aspects of the timing and magnitude of the electrical pulses. In one embodiment, these properties can include, for example, a voltage, a current, or the like. In one embodiment, a first electrical pulse can have a first property and a second electrical pulse can have a second property. This control of the electrical pulses can include the creation of one or several electrical pulse programs, plans, or patterns, and in some embodiments, this can include the selection of one or several pre-existing electrical pulse programs, plans, or patterns. In the embodiment depicted in FIG. 1, the implantable neurostimulation system 100 includes a controller that is a clinician programmer 118. The clinician programmer 118 can be used to create one or several pulse programs, plans, or patterns and/or to select one or several of the created pulse programs, plans, or patterns. In some embodiments, the clinician programmer 118 can be used to program the operation of the pulse generators including, for example, one or both of the external pulse generator 102 and the implantable pulse generator 104. The clinician programmer 118 can comprise a computing device that can wiredly and/or wirelessly communicate with the pulse generators. In some embodiments, the clinician programmer 118 can be further configured to receive information from the pulse generators indicative of the operation and/or effectiveness of the pulse generators and the leads.

In some embodiments, the controller of the implantable neurostimulation system 100 can include a patient remote 120. The patient remote 120 can comprise a computing device that can communicate with the pulse generators via a wired or wireless connection. The patient remote 120 can be used to program the pulse generator, and in some embodiments, the patient remote 120 can include one or several pulse generation programs, plans, or patterns created by the clinician programmer 118. In some embodiments, the patient remote 120 can be used to select one or several of the pre-existing pulse generation programs, plans, or patterns and to select, for example, the duration of the selected one of the one or several pulse generation programs, plans, or patterns.

Advantageously, the above outlined components of the implantable neurostimulation system 100 can be used to control and provide the generation of electrical pulses to mitigate patient pain.

Figure 2:
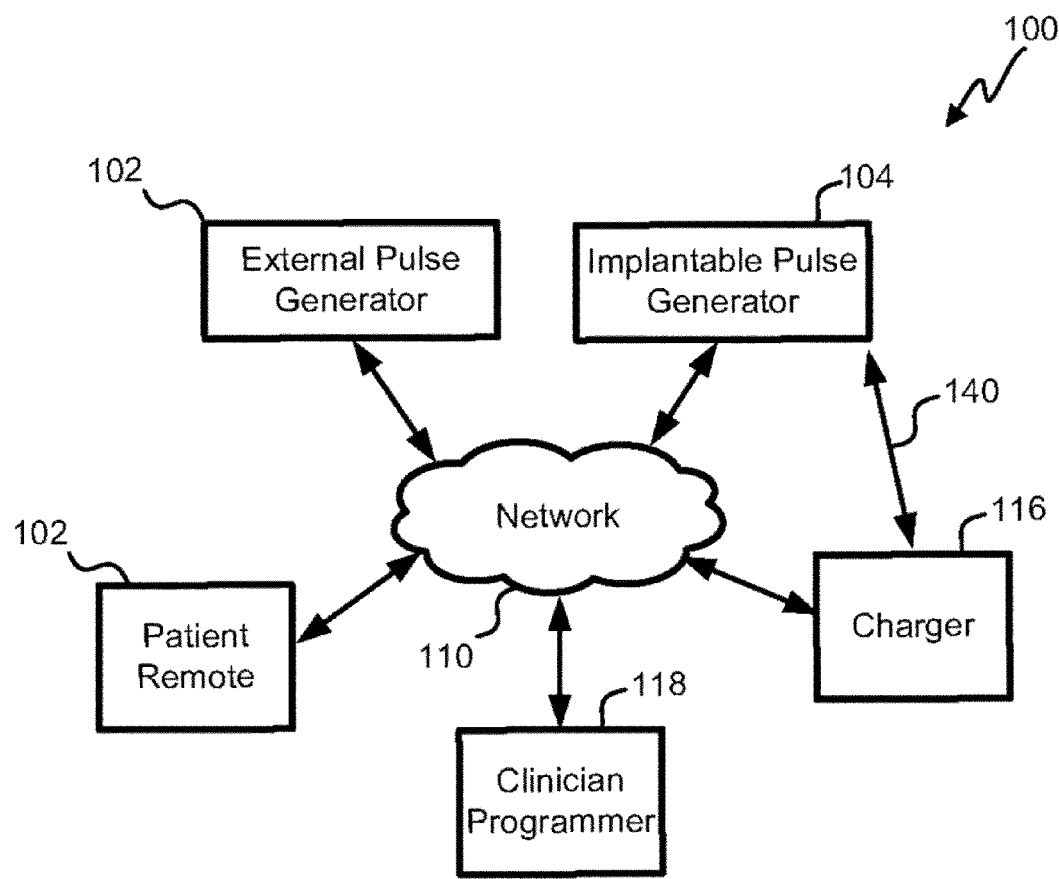
FIG. 2 is a schematic illustration of one embodiment of interconnectivity of the implantable neurostimulation system.

With reference now to FIG. 2, a schematic illustration of one embodiment of interconnectivity of the implantable neurostimulation system 100 is shown. As seen in FIG. 2, several of the components of the implantable neurostimulation system 100 are interconnected via network 110. In some embodiments, the network 110 allows communication between the components of the implantable neurostimulation system 100. The network 110 can be, for example, a local area network (LAN), a wide area network (WAN), a wired network, a custom network, wireless network, a telephone network such as, for example, a cellphone network, the Internet, the World Wide Web, or any other desired network or combinations of different networks. In some embodiments, the network 110 can use any desired communication and/or network protocols. The network 110 can include any communicative interconnection between two or more components of the implantable neurostimulation system 100. In one embodiment, the communications between the devices of the implantable neurostimulation system 100 can be according to any communication protocol including, for example those covered by Near Field Communication (NFC), Bluetooth, or the like. In some embodiments, different components of the system may utilize different communication networks and/or protocols.

As will be described in greater detail below, in some embodiments, the charger 116 can directly communicate with the implantable pulse generator 104, without relying on the network 110. This communication is indicated in FIG. 2 by line 140. In some embodiments, this communication can be accomplished via integrating data transmission functionality into one or several of the components or systems of one or both the charger 116 and the implantable pulse generator 104, or other implantable device. In one particular embodiment, this can be achieved by, for example, incorporating frequency-shift keying ("FSK") capability into the charging systems of one or both of the charger 116 and the implantable pulse generator 104. In one such embodiment, charger 116 would generate a carrier frequency during normal recharging. In the event that communication or other data transmission is desired the carrier frequency can be modulated between two or more frequencies to perform the communication or to transmit the data.

Figure 3:
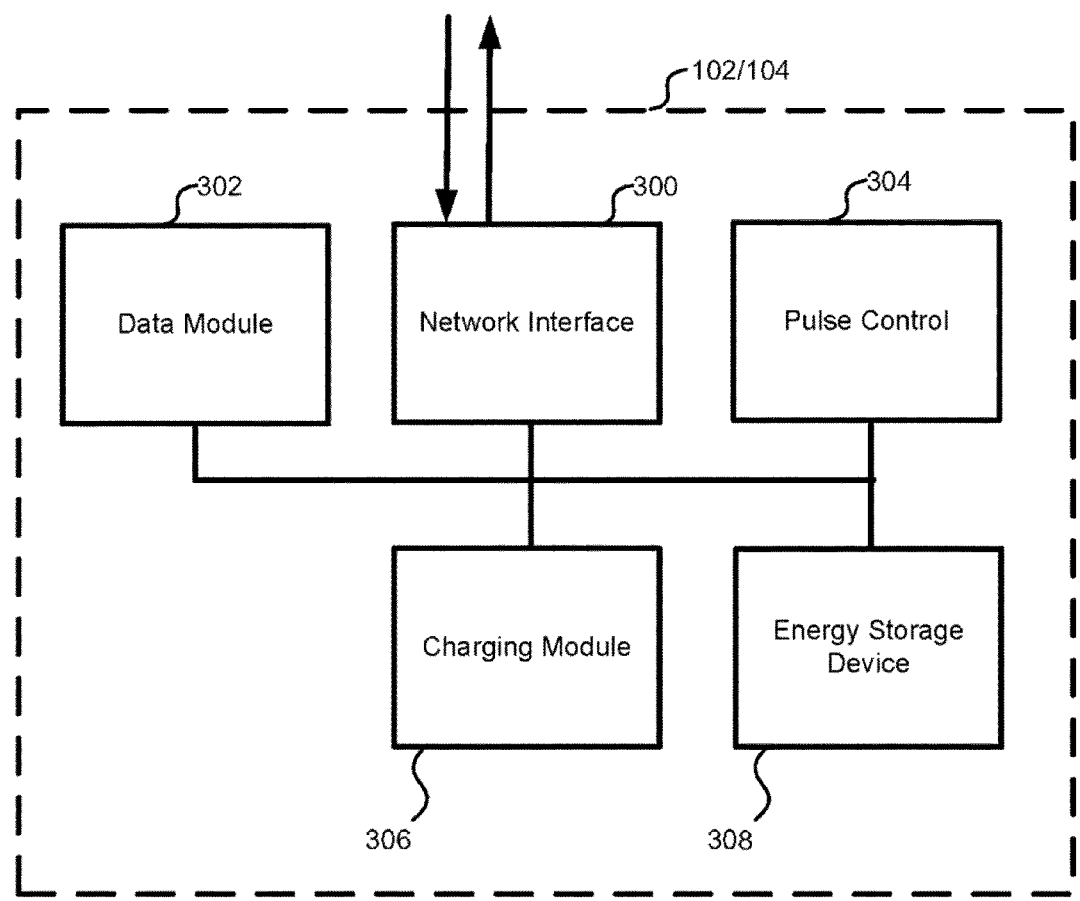
FIG. 3 is a schematic illustration of one embodiment of the architecture of the external pulse generator and/or of the implantable pulse generator that is a part of the implantable neurostimulation system.

With reference now to FIG. 3, a schematic illustration of one embodiment of the architecture of the external pulse generator 102 and/or of the implantable pulse generator 104 is shown. In some embodiments, each of the components of the architecture of the one of the pulse generators 102, 104 can be implemented using the processor, memory, and/or other hardware component of the one of the pulse generators 102, 104. In some embodiments, the components of the architecture of the one of the pulse generators 102, 104 can include software that interacts with the hardware of the one of the pulse generators 102, 104 to achieve a desired outcome.

In some embodiments, the pulse generator 102/104 can include, for example, a network interface 300, or alternatively, a communication module. The network interface 300, or alternatively, the communication module, can be configured to access the network 110 to allow communication between the pulse generator 102, 104 and the other components of the implantable neurostimulation system 100. In some embodiments, the network interface 300, or alternatively, a communication module, can include one or several antennas and software configured to control the one or several antennas to send information to and receive information from one or several of the other components of the implantable neurostimulation system 100.

The pulse generator 102, 104 can further include a data module 302. The data module 302 can be configured to manage data relating to the identity and properties of the pulse generator 102, 104. In some embodiments, the data module can include one or several databases that can, for example, include information relating to the pulse generator 102, 104 such as, for example, the identification of the pulse generator, one or several properties of the pulse generator 102, 104, or the like. In one embodiment, the data identifying the pulse generator 102, 104 can include, for example, a serial number of the pulse generator 102, 104 and/or other identifier of the pulse generator 102, 104 including, for example, a unique identifier of the pulse generator 102, 104. In some embodiments, the information associated with the property of the pulse generator 102, 104 can include, for example, data identifying the function of the pulse generator 102, 104, data identifying the power consumption of the pulse generator 102, 104, data identifying the charge capacity of the pulse generator 102, 104 and/or power storage capacity of the pulse generator 102, 104, data identifying potential and/or maximum rates of charging of the pulse generator 102, 104, and/or the like.

The pulse generator 102, 104 can include a pulse control 304. In some embodiments, the pulse control 304 can be configured to control the generation of one or several pulses by the pulse generator 102, 104. In some embodiments, for example, this information can identify one or several pulse patterns, programs, or the like. This information can further specify, for example, the frequency of pulses generated by the pulse generator 102, 104, the duration of pulses generated by the pulse generator 102, 104, the strength and/or magnitude of pulses generated by the pulse generator 102, 104, or any other details relating to the creation of one or several pulses by the pulse generator 102, 104. In some embodiments, this information can specify aspects of a pulse pattern and/or pulse program, such as, for example, the duration of the pulse pattern and/or pulse program, and/or the like. In some embodiments, information relating to and/or for controlling the pulse generation of the pulse generator 102, 104 can be stored within the memory.

The pulse generator 102, 104 can include a charging module 306. In some embodiments, the charging module 306 can be configured to control and/or monitor the charging/recharging of the pulse generator 102, 104. In some embodiments, for example, the charging module 306 can include one or several features configured to receive energy for recharging the pulse generator 102, 104 such as, for example, one or several inductive coils/features that can interact with one or several inductive coils/features of the charger 116 to create an inductive coupling to thereby recharge the pulse generator 102, 104.

In some embodiments, the charging module 306 can include hardware and/or software configured to monitor the charging of the pulse generator 102, 104. In some embodiments, the hardware can include, for example, a charging coil, which can be, for example, a receiving coil, configured to magnetically couple with a charging coil of the charger 116. In some embodiments, the pulse generator 102, 104 can be configured to receive and/or send data via FSK during charging of the pulse generator 102, 104.

The pulse generator 102, 104 can include an energy storage device 308. The energy storage device 308, which can include the energy storage features, can be any device configured to store energy and can include, for example, one or several batteries, capacitors, fuel cells, or the like. In some embodiments, the energy storage device 308 can be configured to receive charging energy from the charging module 306.

Figure 4:
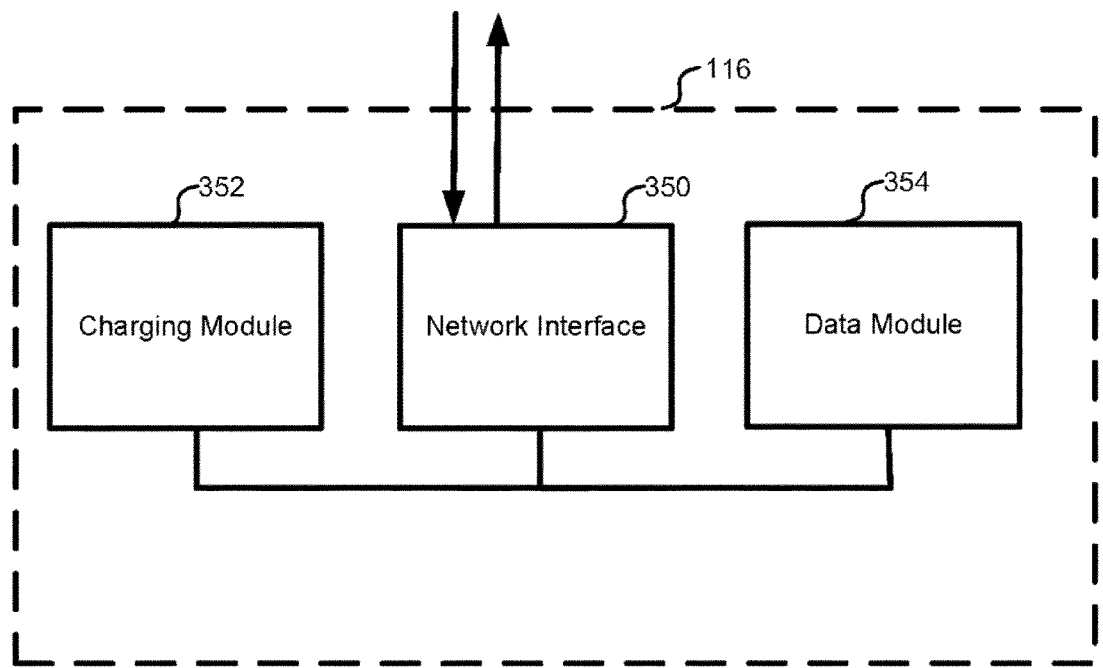
FIG. 4 is a schematic illustration of one embodiment of the charger that is a part of the implantable neurostimulation system.

With reference now to FIG. 4, a schematic illustration of one embodiment of the charger 116 is shown. In some embodiments, each of the components of the architecture of the charger 116 can be implemented using the processor, memory, and/or other hardware component of the charger 116. In some embodiments, the components of the architecture of the charger 116 can include software that interacts with the hardware of the charger 116 to achieve a desired outcome.

In some embodiments, the charger 116 can include, for example, a network interface 350, or alternatively, a communication module. The network interface 350, or alternatively, a communication module, can be configured to access the network 110 to allow communication between the charger 116 and the other components of the implantable neurostimulation system 100. In some embodiments, the network interface 350, or alternatively, a communication module, can include one or several antennas and software configured to control the one or several antennas to send information to and receive information from one or several of the other components of the implantable neurostimulation system 100.

The charger 116 can include a charging module 352. The charging module 352 can be configured to control and/or monitor the charging of one or several of the pulse generators 102, 104. In some embodiments, the charging module 352 can include one or several features configured to transmit energy during charging. In one embodiment, these can include one or several charging coils, which can be, for example, one or several transmitting coils, that can magnetically couple with the charging coil of the pulse generator 102, 104 to thereby recharge the pulse generator 102, 104. In some embodiments, the charging coil can be described by a plurality of parameters including, for example, inductance and/or a quality factor (Q). Similarly, in some embodiments, the magnetic coupling between the transmitting coil and the receiving coil can be described by one or more parameters including, for example, a coupling coefficient.

In some embodiments, charging module 352 of the charger 116 can be configured to send and/or receive data via FSK during charging of the pulse generator 102, 104. The details of these components of the charging module 352 will be discussed in greater detail below.

The charger 116 can include a data module 354. The data module 354 can be configured to manage data for transmission to the pulse generator 102, 104 and/or data received from the pulse generator 102, 104. This information can include, for example, updates to software on the pulse generator 102, 104, pulse patterns, updates relating to the user of the pulse generator 102, 104, or the like. In some embodiments, the data module 354 can be configured to generate transmission data, which can then be communicated to the implantable pulse generator 104. In some embodiments, transmission data is generated by converting data into an encoded form corresponding to the communication capabilities of the charging module 352. In one embodiment in which the charging module 352 can modulate between two frequencies to communicate data, the data can be converted to binary format.

Figure 5:
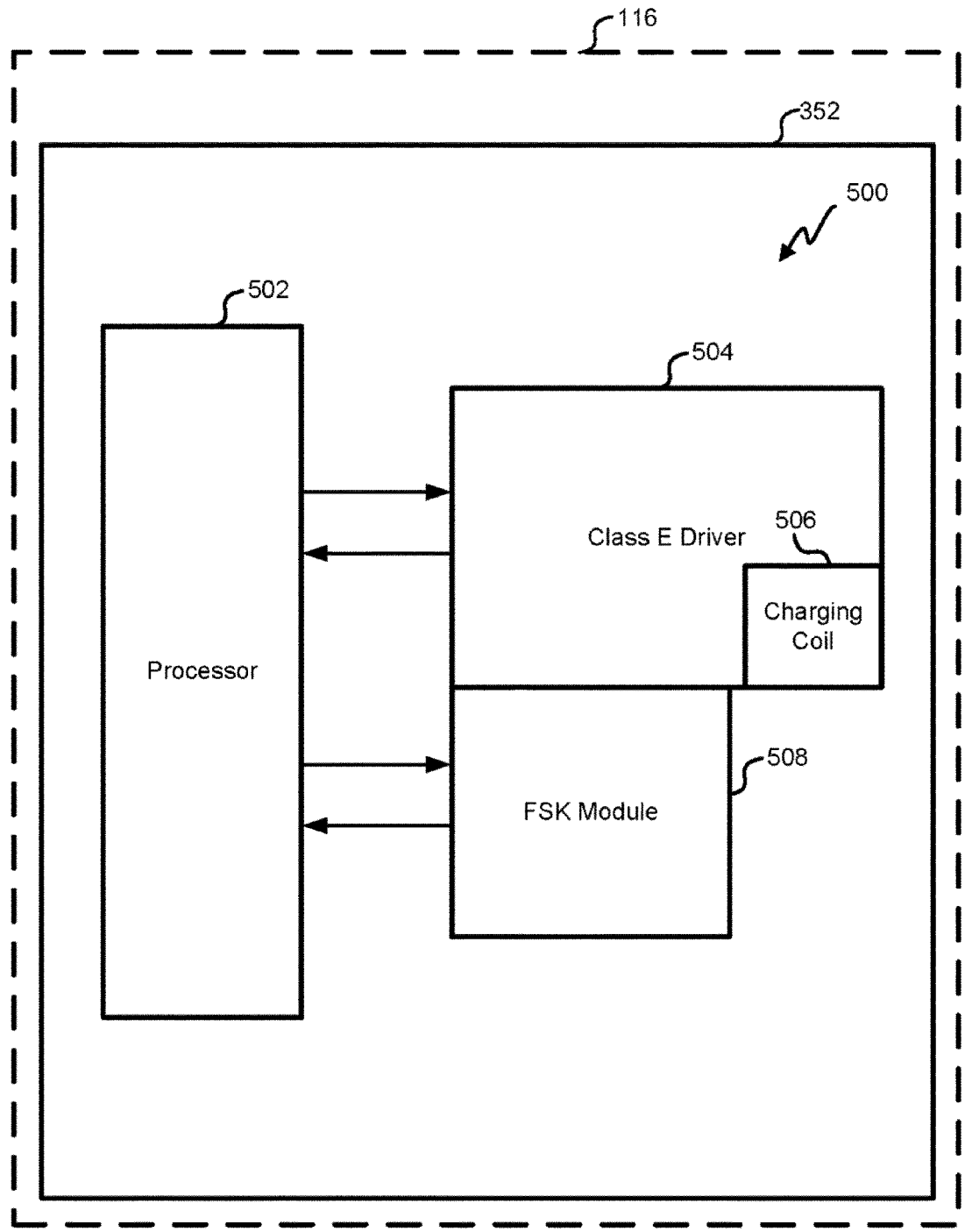
FIG. 5 is a functional block diagram of one embodiment of a charging circuit.

With reference now to FIG. 5, a functional block diagram of one embodiment of the charging circuit 500 of the charging module 352 of the charger 116 is shown. As seen, the charging circuit includes a processor 502, which can correspond to the processor discussed above with respect to charger 116. In some embodiments, the processor 502 can be electrically connected to other components of the charging module 352 to thereby receive signals from these other components of the charging module 352 and to thereby control these other components of the charging module 352.

In some embodiments, and in different circumstances, the charging module 352 may operate at one or several different frequencies. In some embodiments, the processor 502 allows for monitoring the frequency of operation of the charging circuit. In such an embodiment, the processor 502 can be used to control the frequencies of operation of the charging module 352 and to ensure that the frequencies of operation of the charging module are within a desired range or ranges. This can be particularly important in embodiments in which the range of operation frequencies is specified by, for example, a government or government agency. In such embodiments, the processor 502 can ensure operation within regulatory limits and can provide the ability to shut down the charging module 352 if it is operating out of frequency tolerances.

The processor 502 can be connected to a class E driver 504, which can be, for example, a class E type power converter. The class E driver 504 can be used to convert AC to DC. In some embodiments, the class E driver 504, can be an efficient circuit, which efficiency can be obtained by switching an active element (typically a FET, including a MOSFET) of the class E driver 504 fully on or off to thereby avoid the linear region of operation. In some embodiments, this switching can occur when both the voltage and current through the active element are at or near zero. In some embodiments, switching the active element on can occur when the dv/dt across the active element is zero, so that small errors in the switch timing or tuning of the matching network do not significantly degrade the circuit's efficiency. The details of the class E driver 504 will be discussed at greater length below.

As seen in FIG. 5, in some embodiments, the class E driver 504 can include, or be connected with a charging coil 506, which can be a transmitting coil. In some embodiments, the class E driver 504 can be used in powering an implantable device via inductive coupling. In such an embodiment, an inductive coil of the class E driver 504, can serve a dual purpose in functioning as the charging coil 506 while also functioning in a load network of the class E driver 504.

Additionally, in some embodiments, the class E driver can include, or be connected with an FSK module 508. In some embodiments, the FSK module can include one or several features that can be controlled by the processor 508 to modulate and/or change the frequency of the magnetic field created by the charging coil 506. In some embodiments, the FSK module 508 can be controlled to create at least 2 frequencies, at least 3 frequencies, at least 4 frequencies, at least 5 frequencies, and/or any other or intermediate number of frequencies. In one embodiment, the FSK module 508 can be controlled to switch between a first frequency, a second frequency, and a third frequency. In one embodiment, the first frequency can be an intermediate frequency, with the second frequency being a relatively lower frequency and the third frequency being a relatively higher frequency. The details of the FSK module 508 will be discussed at greater length below.

Figure 6:
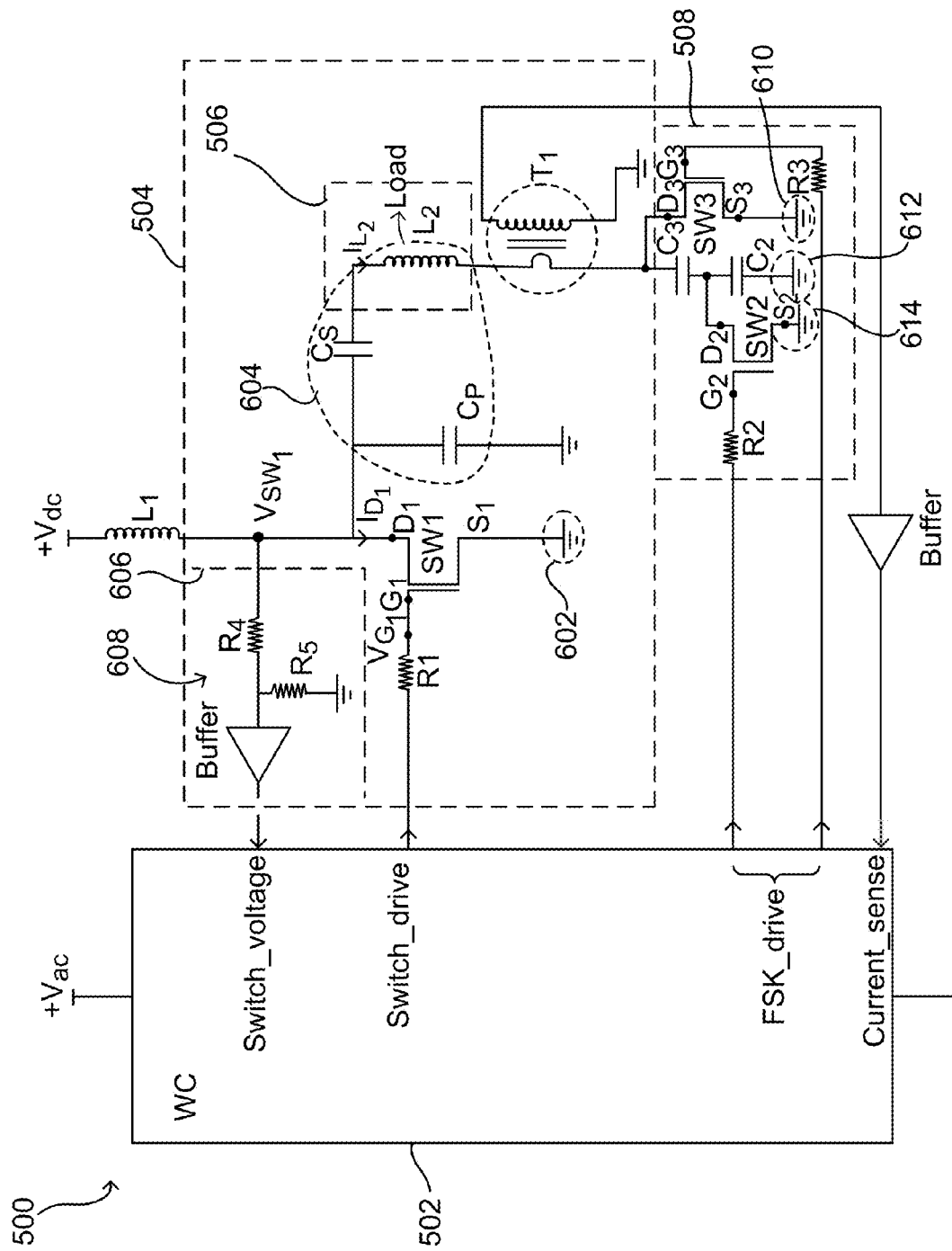
FIG. 6 is schematic illustration of one embodiment of a charging circuit.

With reference now to FIG. 6, a schematic illustration of one embodiment of the charging circuit 500 of the charging module 352 of the charger 116 is shown. As seen in FIG. 6, the charging circuit 500 includes the processor 502, the class E driver 504, the charging coil 506, and the FSK module 508.

The class E driver 504 comprises a power switching transistor (SW1), which can be, for example, a FET transistor. The power switching transistor (SW1) can have a drain (D1) connected to inductor (L1) which acts as a current source to supply DC power to the class E driver 504, a source (S1) connected to ground 602, and a gate (G1) connected to the processor 502. In some embodiments, processor 502 can control the power switching transistor (SW1) by varying the degree to which, or whether a voltage is applied to the gate (G1). The voltage applied to the gate (G1) is identified as drive signal (VG1) in FIG. 6.

The class E driver 504 can include a load matching network 604 that can include capacitors (Cs) and (Cp), and charging coil (L2). In some embodiments, the properties of the load matching network 604, and of capacitors (Cs) and (Cp) and charging coil (L2) can, in combination with other components of the class E driver 504, give the charging circuit 500 a natural frequency, which can be an impulse response frequency.

In some embodiments, and as mentioned above, the charging coil (L2) can be a component of the load matching network 604, and can also be the transmitting coil that magnetically couples with the receiving coil of the implantable pulse generator 104. In such an embodiment, coil current (IL2) passes through charging coil (L2) and creates a magnetic field which can couple with the receiving coil of the implantable pulse generator 104.

The class E driver 504 can include a current sensor (T1) in some embodiments, and as depicted in FIG. 6, the current sensor (T1) can be in series with the charging coil (L2) and can be used to measure the amount of current passing through the charging coil (L2). As depicted in, FIG. 6, the current sensor (T1) can be connected to processor 502 to thereby allow current data generated by the current sensor (T1) to be received by the processor 502. In some embodiments, and as mentioned above, this current data can be used, at least in part, in the generation of control signals by the processor 502.

In some embodiments, the processor 502 can be connected to the class E driver 504 via a switch voltage circuit 606. In some embodiments, the switch voltage circuit 606 can comprise an electrical connection between the drain side of power switching transistor (SW1) and the processor 502. In some embodiments, the switch voltage circuit 606 can comprise features to adjust the voltage measured at the drain side of the power switching transistor (SW1) so that the voltage received at the processor 502 is compatible with the processor 502. In some embodiments, this may include use of an amplifier if the voltage at the drain side of the power switching transistor (SW1) is too low, and in some embodiments, this may include the use of one or several voltage reduction features if the voltage at the drain side of the power switching transistor (SW1) is too high. In the embodiment depicted in FIG. 6, a divider network 608 comprising resistors R4 and R5 is positioned between the drain side of the power switching transistor (SW1) and the processor 502. In some embodiments, the divider network 608 can be further supplemented by a buffer which can further condition the voltage for receipt by the processor 502.

In some embodiments, the processor 502 and the class E driver 504, including the charging coil 506, can operate as follows. Power is supplied to the class E-driver 504 via the inductor (L1), which acts as a current source. Coil current (IL2) is provided to the charging coil (L2), which current produces a magnetic field that can magnetically couple with the receiving coil of the implantable pulse generator 104 to recharge the implantable pulse generator. The load current (IL2) is sensed by the current sensor (T1), and in some embodiments, buffered and squared up, and provided to the processor 502. The processor 502 monitors the zero crossing current transitions of load current (IL2) and adjusts the drive signal (VG1) to the gate (G1) of the switching power transistor (SW1). The use of the processor 502 allows for both the on and off transitions of SW1 to be optimized for efficiency, and allows for these points to change as the operating frequency changes to maintain closer control of the circuit.

In some embodiments, the processor 502 can adjust one or both of the on and off times for power switching transistor (SW1) to maximize efficiency at all conditions of magnetic coupling and external influences on the transmitting coil. For example, if it is desired to switch on power switching transistor (SW1) before the zero crossing signal is received at the processor 502, then the timing can be adjusted for the next cycle based on the last cycle or last few cycles of the feedback signal from current sensor (T1). Additional feedback on circuit operation can also be obtained from the switch voltage circuit 606, which monitors the voltage across the power switching transistor (SW1). In some embodiments, the data from the switch voltage circuit 606 can used to control the power switching transistor (SW1), with a turn on point based on the minimum voltage across the FET. In some embodiments, the switch voltage circuit 606 can be configured to provide feedback on the peak amplitude of the power switching transistor's (SW1) drain voltage, as a check that the class E driver 504 is operating normally and help ensure safe and reliable operation.

In some embodiments, and as depicted in FIG. 6, the charging circuit 500 can include the FSK module 508. The FSK module 508 can include one or several components configured to allow modulation of the natural frequency of the class E driver 504. In some embodiments, these one or several components can be selectively included in, or excluded from the circuit of the class E driver 504 to thereby selectively modulate the natural frequency of the class E driver 504.

In the embodiment depicted in FIG. 6, the FSK module 508 can comprise a second capacitor (C2) and a third capacitor (C3) as well as a second switching transistor (SW2) and a third switching transistor (SW3). In some embodiments, the capacitors (C2, C3) can have any desired properties, and can be any desired capacitors. Similarly, the transistors (SW2, SW3) can have any desired properties and be any desired type of transistors. In some embodiments, the transistors (SW2, SW3) can comprise FET transistors.

In some embodiments, and as depicted in FIG. 6, the FSK module 508 can be configured such that the capacitors (C2, C3) can be selectively electrically included in the charging circuit 500. Specifically, in some embodiments, the processor 502 can be electrically connected to the gates (G2, G3) of the switch transistors (SW2, SW3) to allow the controlled switching of the switch transistors (SW2, SW3). As depicted in FIG. 6, for example, when the third transistor (SW3) is switched to on, the class E driver 504 is connected to ground 610, and none of capacitors (C2, C3) are included in the charging circuit 500. Alternatively, if the second transistor (SW2) is switched to on and the third transistor (SW3) is switched to off, the class E driver 503 is connected to ground 612 and the third capacitor (C3) is included in the charging circuit 500. Finally, if both transistors (SW2, SW3) are switched to off, then the class E driver 504 is connected to ground 614 and both the second and third capacitors (C2, C3) are included in the charging circuit 500. This selective inclusion of the second and third capacitors (C2, C3) in the charging circuit 500 allows the selective modulation between three natural frequencies of the charging circuit, which selective modulation can be used to transmit data from the charger 116 to the implantable pulse generator 104.

Figure 7:
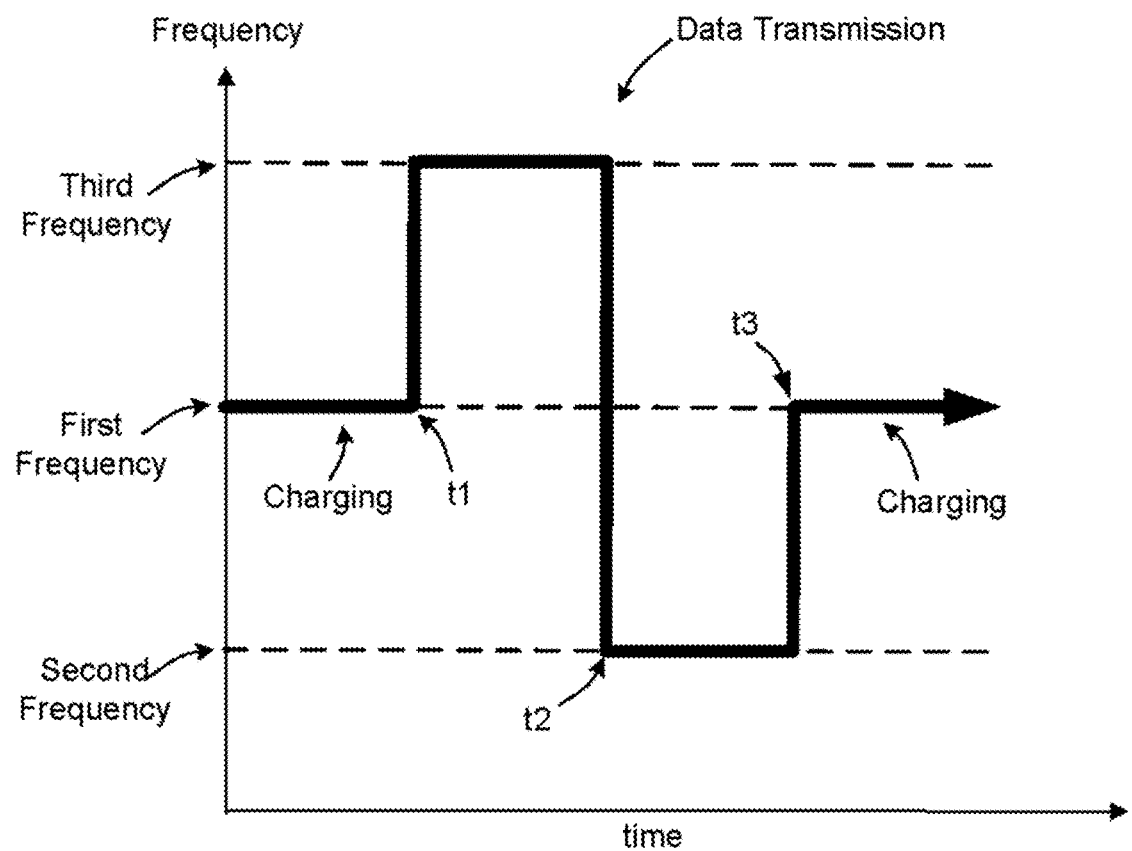
FIG. 7 is a graphical illustration of one embodiment of a transition from a charging mode to a simultaneous charging/data transmission mode.

With reference now to FIG. 7, a graphical illustration of one embodiment of a transition from a charging mode to a simultaneous charging/data transmission mode is shown. In some embodiments in which the charging circuit 500 includes the FSK module 508, the natural frequency of the charging circuit 500 can be modulated to, in addition to recharging the implantable pulse generator 104, communicate with and/or transmit data to the implantable pulse generator 104. In some embodiments, and as depicted in FIG. 7, the FSK module 508 of the charger 116 can be configured to alternate between a first frequency, a second frequency that is lower than the first frequency, and a third frequency that is higher than the first frequency. In some embodiments, the FSK module 508 can configure the charger 116 to generate a magnetic field for recharging the implantable pulse generator 104 at the first, intermediate frequency.

As depicted in FIG. 7, the operation of the charging circuit 500 at the first frequency during the charging mode can continue until time, t1, at which point, the processor 502 controls the FSK module 508 to modulate the natural frequency of the charging circuit 500 to begin transmission of data and to enter into a charging/data transmission mode of operation of the charging circuit 500. As depicted in FIG. 7, this change in modes can begin by modulating the natural frequency of the charging circuit 500 to the third frequency, however, this change in modes can likewise being by modulating the natural frequency of the charging circuit 500 to the second frequency. At time, t2, the processor 502 controls the FSK module 508 to modulate the natural frequency of the charging circuit 500 from the third frequency to the second frequency, and finally, at time, t3, the processor 502 controls the FSK module 508 to modulate the natural frequency of the charging circuit 500 from the second frequency to the first frequency. As depicted, at time, t3, the charging circuit 500 exits the charging/data transmission mode of operation and re-enters the charging mode of operation. In some embodiments, the charging can be performed at an intermediate frequency, which can be a carrier frequency, and the data transmission can be performed by modulating between frequencies that are each either higher or lower than the intermediate frequency.

Figure 8:
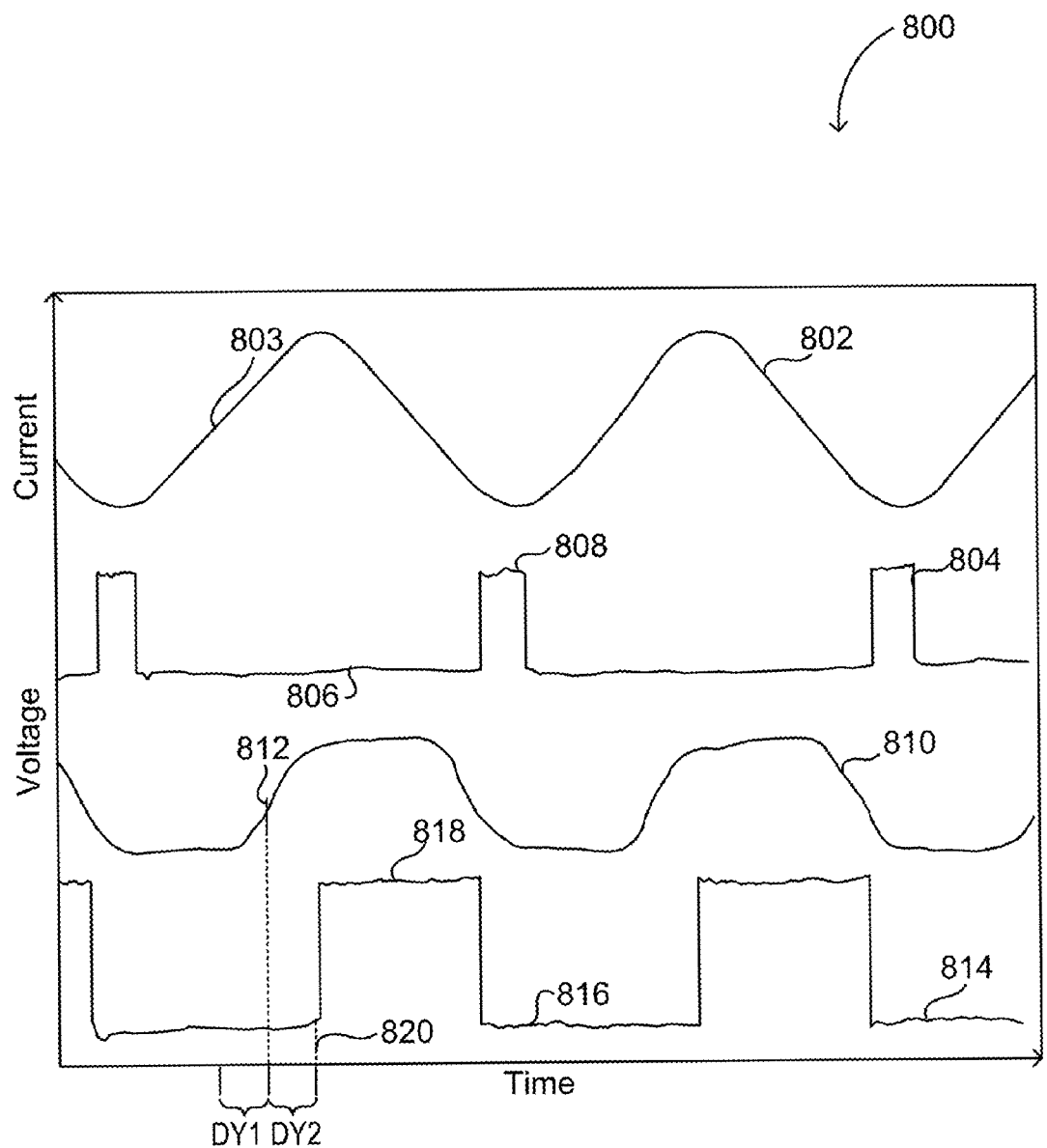
FIG. 8 is a chart illustrating one embodiment of measurements from the charging circuit.

With reference now to FIG. 8, a chart 800 depicting one embodiment of measurements from charging circuit 500 is shown. Chart 800 depicts four traces, a first trace 802 corresponding to the actual coil current (IL2) passing through charging coil (L2) with respect to time. As depicted in chart 800, in some embodiments, the coil current (IL2) can sinusoidally vary with respect to time. Chart 800 further identifies the time 803 at which one of the several zero crossing current transitions of the coil current (IL2) passing through the charging coil (L2) occurs.

Chart 800 depicts a second trace 804 that corresponds to the drive signal (VG1). As seen in chart 800, the drive signal (VG1) can comprise a repeated boxcar function. In some embodiments, the second trace can comprise a first position 806, at which position the power switching transistor (SW1) is open, and a second position 808, at which position the power switching transistor (SW1) is closed. In some embodiments, the drive signal (VG1) can be characterized by a frequency with which the subsequent second position 808 corresponding to the power switching transistor (SW1) closed times occurs, and a length of time in which the drive signal (VG1) remains in the second position 808.

Chart 800 depicts a third trace 810 that corresponds to the current sensed by current sensor T1, with voltage clamping applied. As seen, the combination of this current output and the voltage clamping results in a periodic, truncated function. Chart 800 identifies the time 812 at which the current sensor T1 senses the zero crossing current transition of time 803. As seen, time 803 and time 812 are separated by a propagation delay (DY1).

Chart 800 depicts a fourth trace 814 that corresponds to the output from the buffer to T1 and input into the processor 502. This fourth trace 814 further corresponds to buffer affected output based on the third trace 810. The fourth trace 814 can be a repeated boxcar function having a first level 816 and a second level 818. As seen in chart 800, time 820 identifies the instant of the first transition from the first level 816 to the second level 818 after the zero crossing current transition of the coil current (IL2) at time 803. The temporal separation between time 820 and time 812 is propagation delay (DY2).

Figure 9:
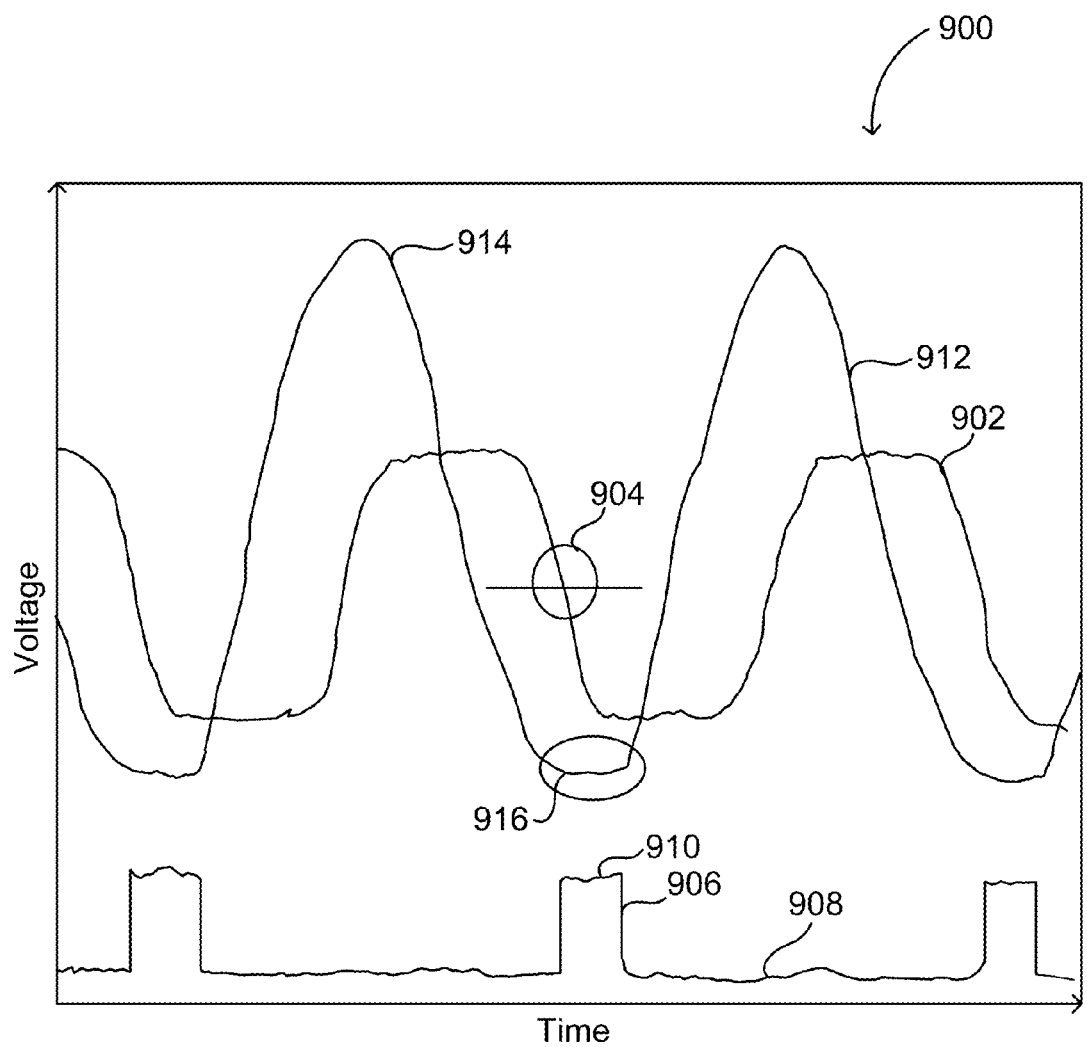
FIG. 9 is a chart illustrating one embodiment of measurements from the charging circuit when the switching time is properly tuned.

In addition to delays (DY1, DY2), two additional propagation delays arise in the operation of charging circuit 500. In one embodiment, these delays can include (1) processing time taken by the processor 502, and (2) the turn-on time of the power switching transistor (SW1). In some embodiments, these propagation delays can adversely affect the operation of the charging circuit 500, because immediate correction of improper timing cannot be made using presently utilized control methods. In the prior art, by the time the need for a timing change is identified, the proper time to make that change has passed. In one embodiment, and to counteract these propagation delays, the processor 502 can comprise a table identifying different frequencies for drive signal (VG1) and/or different lengths of time in which the drive signal (VG1) can remain in the second position 808. In some embodiments, the values in this table can be generated during evaluation of the charging circuit 500 under different load conditions which can, for example, replicate different magnetic couplings with the implantable pulse generator. By using processor control to implement a change in drive signal timing, which results in a change of the frequency of the drive signal (VG1) and/or different lengths of time in which the drive signal (VG1) is in the second position 808, the drive signal enters the second position 808 in the next (or later) cycle of the coil driving circuit, such as shown in FIG. 9 below. By this, any propagation delays such as those identified above are inherently compensated for in the next (or later) cycle, and do not compromise the transmitter operating efficiency.

Figure 10:
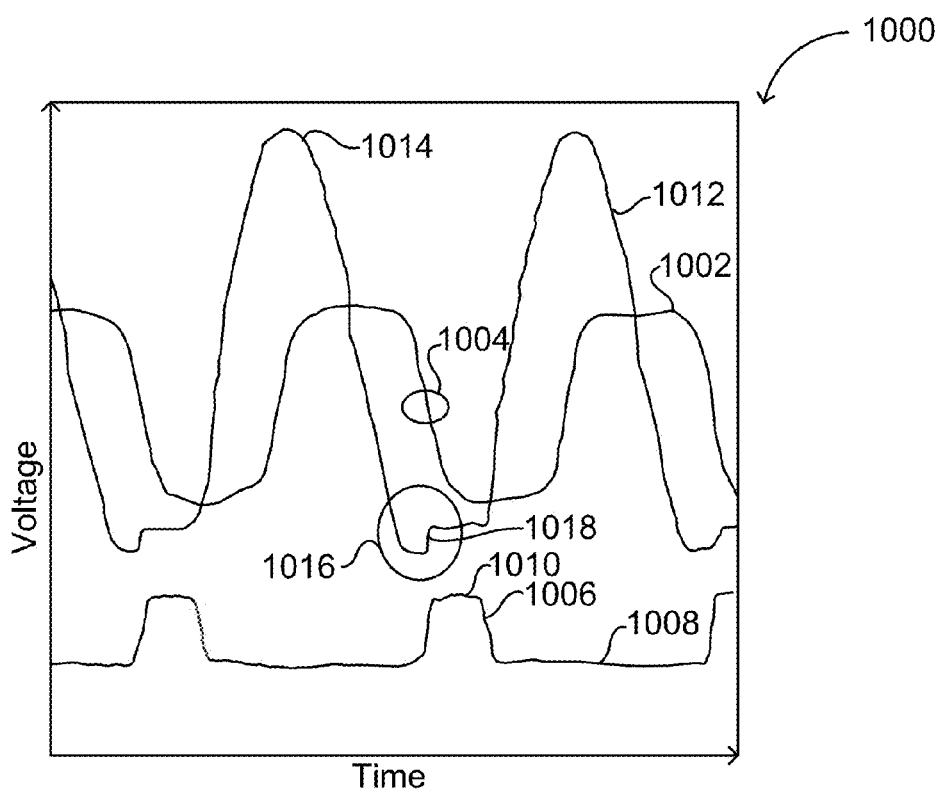
FIG. 10 chart illustrating one embodiment of measurements from the charging circuit when the switching time is too slow.
Figure 11:
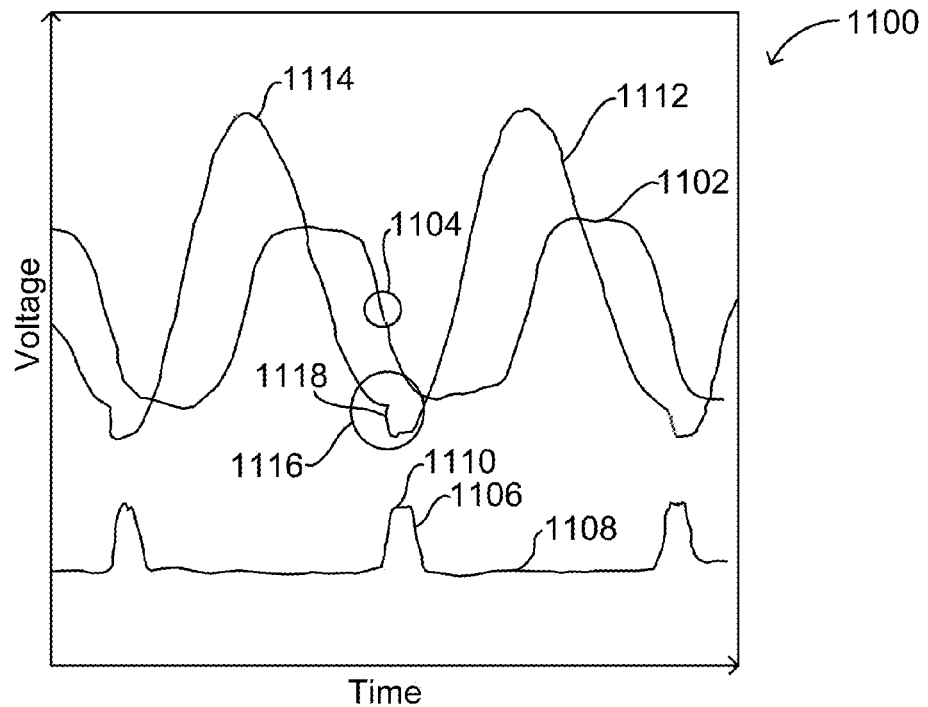
FIG. 11 is a chart illustrating one embodiment of measurements from the charging circuit when the switching time is too fast.

FIGS. 9-11 depict charts 900, 1000, 1100 showing the impact of different drive signal frequencies on the operation of charging circuit 500. Specifically, chart 900 depicts a first trace 902 corresponding to the current sensed by current sensor T1, with voltage clamping applied. As seen, the combination of this current output and the voltage clamping results in a periodic, truncated function. Chart 900 identifies the time 904 at which the current sensor T1 senses the zero crossing current transition.

Chart 900 depicts a second trace 906 that corresponds to the drive signal (VG1). As seen in chart 900, the drive signal (VG1) can comprise a repeated boxcar function. In some embodiments, the second trace 906 can comprise a first position 908, at which position the power switching transistor (SW1) is open, and a second position 910, at which position the power switching transistor (SW1) is closed. In some embodiments, the closing of the power switching transistor (SW1) can connect the drain (D1) to ground 602 via source (S1). This connection can drive the voltage across the power switching transistor (SW1) to zero.

Chart 900 further depicts a third trace 912 corresponding to the sensed voltage across power switching transistor (SW1). The third trace 912 has a first, sinusoidal portion 914, and a second, flat portion 916. In some embodiments, the first, sinusoidal portion 914 of the third trace 912 indicates the varying voltage across the power switching transistor (SW1), and the second, flat portion 916 can identify the voltage across the power switching transistor (SW1) after the power switching transistor (SW1) is closed, which voltage, in the embodiment of FIG. 6, is zero. In some embodiments, in which the frequency of the drive signal (VG1) is properly tuned for the condition of the charging circuit 500, the second, flat portion 916 of the third trace 912 can be flat, or in other words, without a step.

Chart 1000 of FIG. 10 depicts one embodiment of traces of the same properties of chart 900, but in which the frequency of the drive signal (VG1) is too low, and the power switching transistor (SW1) is switched too late. Specifically, chart 1000 depicts a first trace 1002 corresponding to the current sensed by current sensor T1, with voltage clamping applied and identifying the time 1004 at which the current sensor T1 senses the zero crossing current transition. Chart 1000 further identifies a second trace 1006 that corresponds to the drive signal (VG1). This second trace 1006 includes a first position 1008, at which position the power switching transistor (SW1) is open, and a second position 1010, at which position the power switching transistor (SW1) is closed.

Chart 1000 depicts a third trace 1012 corresponding to the sensed voltage across power switching transistor (SW1). The third trace 1012 has a first, sinusoidal portion 1014, and a second, flat portion 1018. As seen in chart 1000, as the frequency of the drive signal (VG1) is too low, the voltage indicated by the third trace 1012 drops below zero before the power switching transistor (SW1) is closed, and jumps via step 1018 to a zero voltage when the power switching transistor (SW1) is closed.

Chart 1100 of FIG. 11 depicts one embodiment of traces of the same properties of chart 900, but in which the frequency of the drive signal (VG1) is too high, and the power switching transistor (SW1) is switched too early. Specifically, chart 1100 depicts a first trace 1102 corresponding to the current sensed by current sensor T1, with voltage clamping applied and identifying the time 1104 at which the current sensor T1 senses the zero crossing current transition. Chart 1100 further identifies a second trace 1106 that corresponds to the drive signal (VG1). This second trace 1106 includes a first position 1108, at which position the power switching transistor (SW1) is open, and a second position 1110, at which position the power switching transistor (SW1) is closed.

Chart 1100 depicts a third trace 1112 corresponding to the sensed voltage across power switching transistor (SW1). The third trace 1112 has a first, sinusoidal portion 1114, and a second, flat portion 1118. As seen in chart 1100, as the frequency of the drive signal (VG1) is too high, the voltage indicated by the third trace 1012 does not reach zero before the power switching transistor (SW1) is closed, and jumps via step 1118 to a zero voltage when the power switching transistor (SW1) is closed. In the embodiments of FIGS. 10 and 11 the efficiency of the charging circuit is adversely affected by the frequency of the drive signal (VG1) being either too low or too high.

Figure 12:
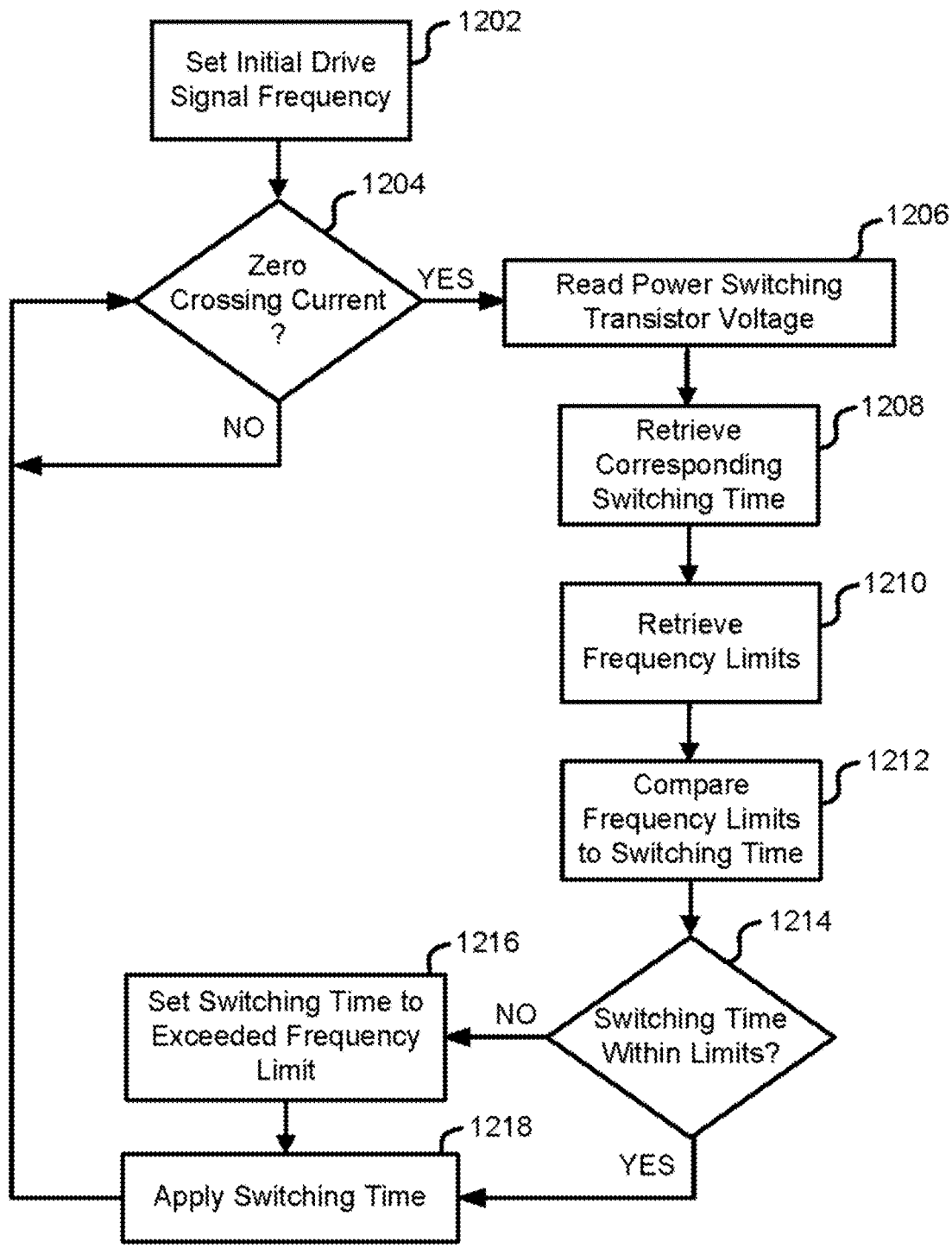
FIG. 12 is a flowchart illustrating one embodiment of a process for controlling the switching time of a charging circuit.

With reference now to FIG. 12, a flowchart illustrating one embodiment of a process 1200 for controlling the frequency of a charging circuit 500 is shown. The process begins at block 1202, wherein an initial frequency of the drive signal (VG1) is set. In some embodiments, this initial frequency can be a default frequency that can be, for example, stored in the memory of the charger 116 and/or other component of the implantable neurostimulation system 100.

After the initial frequency of the drive signal (VG1) is set, the process 1200 proceeds to decision state 1204, wherein it is determined if a current zero-crossing transition has occurred. In some embodiments, this determination can be made based on data received from the current sensor (T1). If it is determined that no current zero-crossing transition has occurred, the process 1200 waits a length of time which length of time can be, for example, predetermined, and then returns to decision state 1204.

If it is determined that a current zero-crossing transition has occurred, the process 1200 proceeds to block 1206 wherein the power switching transistor voltage is sensed or read. In some embodiments, this voltage can be read from the switch voltage circuit 606. In some embodiments, the reading of the power switching transistor voltage can include determining whether the voltage at the power switching transistor (SW1) at the instant before and/or of the closing of the power switching transistor (SW1) is greater than, less than, or equal to the voltage at the power switching transistor (SW1) after the closing of the power switching transistor (SW1). In some embodiments, the voltage of the power switching transistor can be read at a first time that corresponds to the current zero-crossing.

After the power switching transistor voltage has been read, the process 1200 proceeds to block 1208 wherein the switching time corresponding to the read power switching transistor voltage is read. In some embodiments, this switching time can be the frequency of the drive signal (VG1). The switching time can be read from an entry in a table of switching times, which table of switching times can be generated by analyzing the charging circuit 500 under a variety of circumstances and load conditions. In some embodiments, this step can result in retrieving a value for adjusting the frequency of the drive signal (VG1) to more closely match the properties and/or load conditions of the charging circuit 500.

After the switch time corresponding to the read voltage of the power switching transistor (SW1) is retrieved, the process 1200 proceeds to block 1210, wherein frequency limits are retrieved. In some embodiments, the frequency limits can correspond to one or several limits on the frequencies of operation of the charging circuit 500 such as, for example, one or several legal limits, regulatory limits, or the like. In one embodiment, for example, the frequency limits can correspond to one or both of an upper limit (high limit) and a lower limit (low limit).

After the frequency limits have been retrieved, the process 1200 proceeds to block 1212, wherein the frequency limits are compared to the retrieved corresponding switching time. In some embodiments, this comparison can be performed by the processor of the charger 116. After the frequency limits are compared to the switching time, the process 1200 proceeds to decision state 1214, wherein it is determined if the retrieved corresponding switching time is within the frequency limits. This comparison can be performed by the processor of the charger 116.

If it is determined that the retrieved corresponding switching time is not within the frequency limits, the process 1200 proceeds to block 1216, wherein the switching time is set to one of the upper and lower frequency limits. In some embodiment, the one of the upper and lower frequency limits can be whichever of the upper frequency limit and the lower frequency limit is implicated in decision state 1214. After the switching time has been set to one of the upper and lower frequency limits, or returning to decision state 1214, if it is determined that the switching time is within the frequency limits, then the process 1200 proceeds to block 1218, wherein the switching time is applied in that the frequency of the drive signal (VG1) is set to the retrieved corresponding switching time. After the switching time has been applied, the process 1200 returns to decision state 1204, and proceeds as outlined above. In some embodiments, and as is the case with propagation delays, the cycle can be repeated multiple times until a switching time is identified that mitigates the propagation delays and corresponds to the functioning of the charging circuit 500. In some embodiments, and after a switching time has been identified that satisfactorily mitigates the propagation delays and/or the effects of the propagation delays, the charging circuit 500 can be operated at a steady state at that switching time.

In the foregoing specification, the invention is described with reference to specific embodiments thereof, but those skilled in the art will recognize that the invention is not limited thereto. Various features and aspects of the above-described invention can be used individually or jointly. Further, the invention can be utilized in any number of environments and applications beyond those described herein without departing from the broader spirit and scope of the specification. The specification and drawings are, accordingly, to be regarded as illustrative rather than restrictive. It will be recognized that the terms "comprising," "including," and "having," as used herein, are specifically intended to be read as open-ended terms of art.

What is claimed is:

1. A portable charger device for transcutaneous charging of an implantable neurostimulator in a patient, the charger device comprising:
    a housing having an external surface that is configured to at least partially engage a skin surface of the patient and be positioned at least partially over the implantable neurostimulator;
    a charging coil disposed within the housing, wherein the charging coil is configured to generate a magnetic field having a frequency and to magnetically couple with the implantable neurostimulator to recharge the implantable neurostimulator;
    a class E driver disposed within the housing and electrically coupled to the charging coil, wherein the class E driver comprises:
        a switching circuit, wherein the switching circuit is switched by the application of a first voltage to the switching circuit;
        a current sensor positioned to sense a current passing through the charging coil;
        an FSK module configured to modulate the frequency of the magnetic field among at least three frequencies; and
    a processor disposed within the housing and electrically coupled to the class E driver, wherein the processor is configured to receive data indicative of the current passing through the charging coil and control the switching circuit via the application of the first voltage to the switching circuit in response to the received data, wherein the processor is configured to selectively operate the charger in either a data non-transmitting state or in a data transmitting state, wherein a carrier signal has the first frequency when the charger operates in the data non-transmitting state, and wherein the processor controls the FSK module to modulate the carrier signal between the second frequency and the third frequency when the charger operates in the data transmitting state.

2. The portable charger device of claim 1, wherein the FSK module allows modulation between 3 different frequencies so as to improve efficiency of data transmission simultaneous with recharging.

3. The portable charger device of claim 1, wherein the processor is configured to control the FSK module to modulate the frequency of the magnetic field.

4. The portable charger device of claim 3, wherein the FSK module comprises two capacitors and two transistors, wherein the two transistors are controllably connected to the processor such that the two capacitors can be selectively included within the circuit by the FSK module to modulate the frequency of the magnetic field between the first, second, and third frequencies.

5. The portable charger device of claim 1, wherein the processor is electrically connected to the class E driver to receive data indicative of a second voltage of the switching circuit.

6. The portable charger device of claim 5, wherein the processor is further configured to:
   receive data indicative of the second voltage of the switching circuit; and
   control the switching circuit in response to the received data indicative of the second voltage of the switching circuit.

7. The portable charger device of claim 1, wherein the processor is configured to:
   sense a power switching transistor voltage; and
   determine whether to adjust a first frequency with which the first voltage is applied to the switching circuit, wherein the adjustment of the first frequency mitigates one or several propagation delays.

8. The portable charger device of claim 7, wherein the processor is configured to retrieve a stored value identifying a second frequency with which the first voltage is applied based on the sensed power switching transistor voltage.

9. The portable charger device of claim 8, wherein the processor is configured to compare the retrieved stored value identifying the second frequency with which the first voltage is applied to one or several frequency limits.

10. The portable charger device of claim 9, wherein the first frequency is set to the second frequency if the second frequency does not exceed the one or several frequency limits.

11. The portable charger device of claim 9, wherein when the second frequency exceeds one of the one or several frequency limits, the first frequency is set to the exceeded one of the one or several frequency limits.

12. A method of controlling transcutaneous charging of an implantable neurostimulator in a patient with a charger device, the method comprising:

magnetically coupling the charger device and the implantable neurostimulator, wherein the magnetic coupling of the charger device with the implantable neurostimulator charges the implantable neurostimulator;

setting an initial frequency of a drive signal, wherein the initial frequency of the drive signal is set by a processor, and wherein the drive signal controls opening and closing of a switch;

identifying a time of a current zero-crossing transition;

sensing a voltage at the switch at the time of the current zero-crossing transition;

retrieving a value identifying a second frequency based on the voltage at the switch at the time of the current zero-crossing transition; and changing the frequency of the drive signal.

13. The method of claim 12, wherein changing the frequency of the drive signal comprises changing the frequency of the drive signal from the first frequency to the second frequency.

14. The method of claim 13, comprising retrieving one or several frequency limits, wherein the frequency limits provide an upper and lower bound to a range of acceptable frequencies of the drive signal.

15. The method of claim 14, comprising comparing the second frequency to the one or several frequency limits.

16. The method of claim 15, wherein changing the frequency of the drive signal comprises changing the frequency of the drive signal from the first frequency to the one of the one or several frequency limits if the second frequency exceeds the one of the one or several frequency limits.

17. The method of claim 15, wherein changing the frequency of the drive signal comprises changing the frequency of the drive signal from the first frequency to the second frequency if the second frequency does not exceed the one or several frequency limits.

18. The method of claim 17, further comprising modulating the frequency of the drive signal with an FSK module to transition between a data transmitting state and a data non-transmitting state.

* * * * *